(12) United States Patent
Ala-Kleme et al.

(10) Patent No.: US 7,005,108 B2
(45) Date of Patent: Feb. 28, 2006

(54) INSULATOR ELECTRODE DEVICES

(75) Inventors: Timo Ala-Kleme, Mellilä (FI); Philip Canty, Cork (IL); Jarkko Eskola, Turku (FI); Timo Korpela, Turku (FI); Sakari Kulmala, Kirkkonummi (FI); Piia Vainio, Turku (FI)

(73) Assignee: Labmaster Ltd., Turku (FI)

( * ) Notice: Subject to any disclaimer, the term of this patent is extended or adjusted under 35 U.S.C. 154(b) by 390 days.

(21) Appl. No.: 10/128,571

(22) Filed: Apr. 24, 2002

(65) Prior Publication Data

US 2003/0192780 A1   Oct. 16, 2003

(30) Foreign Application Priority Data

Apr. 15, 2002   (FI)   .................................. 20020724

(51) Int. Cl.
*G01N 21/29* (2006.01)
(52) U.S. Cl. .................. 422/82.05; 204/291; 204/409; 204/416; 204/419
(58) Field of Classification Search ................ 204/291, 204/416, 419, 409; 422/82.05
See application file for complete search history.

(56) References Cited

U.S. PATENT DOCUMENTS

| 4,835,059 | A | 5/1989 | Kadato |
| 5,980,977 | A | 11/1999 | Deng et al. |
| 6,136,268 | A | 10/2000 | Ala-Kleme et al. |
| 6,251,690 | B1 * | 6/2001 | Kulmala et al. ............ 436/518 |

* cited by examiner

*Primary Examiner*—Bruce F. Bell
(74) *Attorney, Agent, or Firm*—Armstrong, Kratz, Quintos, Hanson & Brooks, LLP

(57) ABSTRACT

Methods and insulator electrode devices for performing electrochemical reactions are disclosed. The devices consist of high specific surface area electrodes based on a channeled conducting base material that has been coated with an organic or inorganic insulating film or multiple layers of such films. The chemical reactions are exemplified by exciting one or several label compounds into an excited state which is spontaneously de-excited by emission of ultraviolet, visible or infrared light, in aqueous solution. This provides the basis for reproducible analytical applications in bioaffinity assays such as immunoassays and DNA-probing assays.

9 Claims, 14 Drawing Sheets

(a)

(b)

20020102A/JUE

INSULATOR ELECTRODE DEVICES

BACKGROUND OF INVENTION

1. Field of Invention

The present invention relates to hot electron-operated electrochemical reactors which are applied to carry out chemical reactions. The device comprises working electrode/electrodes which are coated according to the prior art with an electrically insulating layer, which enables to carry out non-conventional electrochemical redox reactions. The electrode device has a wide area of application as a chemical reactor, in analytical chemistry, and in biochemistry as a sensitive detector, in particular, with methods based on biorecognition, such as in clinical diagnostics.

2. Description of the Related Art

A considerable improvement over the active metal or semiconductor electrodes used to carry out different electrochemical reactions was provided by the publication WO 98/36266 (U.S. Pat. No. 6,251,690 Kulmala et al.). These so-called insulating film-coated electrodes can be applied to the generation of exceptional chemical reactions at high redox energy levels. When such electrode reactions are effected in the presence of certain organic or inorganic luminophores, light is generated. Whereas a variety of applications based on this phenomenon can be readily advised, one of the most evident one is the use of such a system as a sensitive detector in analytical chemistry as described in WO 98/36266.

Many commercially important analytical methods require sensitive and specific detectors. The majority of such methods are based on the principle that the analytes are separated by their biological function and thereafter quantified using certain label substances. For instance, in the assays based on the biological properties of analytes, such as in immunoassays, the analyte (A) can be selectively captured from a solution upon a solid support with the aid of antibodies immobilized on the surface of the solid support, and the amount of (A) can be quantified using another antibody selectively binding with (A) and being labeled with a suitable marker substance. Such a marker substance can be, for instance, a radioactive isotope, an enzyme, a molecule that absorbs light or produces fluorescence or phosphorescence, certain metal chelates etc., which can be coupled with an antibody via chemical bonds. Alternatively, purified (A) can be labeled (A-L) and the amount of unlabeled (A) can be determined by antibodies immobilized on a solid support by exploiting a competitive reaction between (A-L) and analyte (A). DNA- and RNA-probing assays are based on analogous bioaffinity principles to those of immunoassays and can be performed along with related procedures. Also, other chemical and biochemical analysis methods can be based on analogous principles. Presently, there is an increasing need for multiparameter assays due to a growing demand to decrease the costs and/or increase the simplicity and accuracy of determinations. One solution to these problems is the use of label compounds which luminesce at different wavelengths. Various methods and strategies in immunoassays are described, e.g., in "The Immunoassay Handbook", Edited by David Wild, Stockton Press Ltd., New York, 1994, pages 1–618.

Totally new, strongly commercially emerging technologies are also based on the exploitation of biorecognition. This is called DNA microarray technology and has attracted tremendous interests among biologists. It is widely known that thousands of genes and their products (i.e. RNAs and proteins) in a given living organism function in a complicated and orchestrated way. Traditional methods of molecular biology generally work on a "one gene in one experiment" basis, which means that the "whole picture" of a gene function is hard to obtain. The new DNA microarray technology promises to monitor the whole genome on a single chip so that interactions among thousands of genes can be investigated simultaneously. Terminologies that have been used in the literature for such a device, include, but are not limited to: biochip, DNA chip, gene chip, DNA microarray, gene array, and genome array. For RNA and proteins, the related techniques are called RNA microarray and proteomics, respectively. The commercial applications of DNA microarray technology include gene discovery, disease diagnostics (commercially the most important), drug discovery, and toxicology.

The present technical level of the microarray technologies are exemplified by the following articles: M. Schena et al., Trends in Biotechnology, 1998, 16, 301–306; G. MacBeath and S. Schreiber, Science, 200, 289(5485), 1760–1763; and G. Ramsay, Nature Biotechnology, 1998, 16, 40–44.

These new technologies demand extremely high sensitivities and flexibilities of the detector systems, while at the same time the dimensions must be miniaturized to an utmost minimum.

It is already known that organic luminophores and metal chelates suitable for labeling in analytical methods can be excited with light or by electrochemical means resulting in the specific emission of light from the labeling substance. The methods based on these phenomena are generally sensitive and well-suited for the excitation of label substances. However, difficulties are encountered when the concentrations of labels in real assays are very low; e.g., the use of fluorescence is complicated by the existence of Tyndall, Raleigh, and Raman scattering, and by the background fluorescence common in biological samples. Phosphorescence in liquid phase is mainly usable only in connection with some specially synthesized lanthanide chelates. Utilization of the long-lived photoluminescence of these compounds is restricted mainly due to the complicated apparata required and high cost of pulsed light sources.

Electrochemiluminescence can be generated in non-aqueous solvents at inert metal electrodes with a rather simple apparatus. However, certain chemical reactions like bioaffinity assays which are of commercial importance are normally applicable in aqueous solutions only. Samples are practically always aqueous and therefore the detection method of a label substance must be applicable in aqueous solution. Presently, only certain transition metal chelates can serve as electrochemiluminescent labels in micellar solutions, which, in fact, are to be considered at least partly as non-aqueous solutions. However, these methods utilizing conventional electrochemistry and inert metal electrodes do not allow simultaneous excitation of several label substances possessing sufficiently differing emission spectra and/or luminescence lifetime.

Mainly inert active metal electrodes are applied in conventional electrochemistry. Their utilization is restricted to a narrow potential window due to the water decomposition reactions, resulting in hydrogen and oxygen evolution. Luminophores usable as fluorescent or phosphorescent labels cannot normally be electrically excited in aqueous solution at these electrodes due to the inaccessibility of the highly anodic and cathodic potentials required for the excitation reactions. With suitably selected semiconductor electrodes, a wider potential window is achievable, but only very rare labeling substances can be excited at these type of electrodes in fully aqueous solutions. A considerable improvement for the use of active metal electrodes or semiconductor electrodes was provided by WO 98/36266 (Kulmala et al.) which made it possible to simultaneously excite a variety of different labeling substances in a fully aqueous solution. This invention by Kulmala et al. utilized a new type of electrochemistry and electrodes, conductors covered with a thin insulating film, which cannot be used in conventional electrochemistry. These electrodes are called insulator electrodes or insulating film-coated electrodes. According to the present invention, is was suprisingly observed that their performance and applicability is considerably improved by constructing a channeled texture of the electrode surfaces.

As a technical construction, two patent publications, WO 99/09042 and WO 99/33559 describe microfabricated devices used for chromatographic separation and concentration of different substances. Although certain technical features, like micropores or channels, disclosed in said publications resemble those used in the present invention, their meaning and applications are completely different. In the present invention, microstructures are created on electrode devices to be used for carrying out electrogenerated chemical reactions in the vicinity of the electrode surfaces based on the hot electron-induced mechanism. The main application of the electrode device of the present invention is its use as an electrochemical detector with a photomultiplier tube or photodiode. In the future, various other applications based on this novel electrochemistry will be expected. A drawback of utilizing the insulating film-coated electrodes disclosed in WO 98/36266, was the relatively long assay times due to the macro-scale cells employed and the low specific surface areas of the working electrodes, which affects the sensitivity and the applicability of such electrodes. In theory, the insulating film-coated electrodes work in relatively simple systems. However, the electrodes, as described in the prior art, are useful only for limited applications and do not fullfil the requirements of the most modem trends in the development of analytical chemistry. The electrodes are not sensitive enough for the most demanding modern applications and they are not essentially suitable for functioning as flow-through detectors because they were mainly aimed at application to batch assays. The most severe drawback when using said electrodes is the very high diffusion times of the biorecognition reactions on the macro-scale electrodes. Further, although the simple insulator electrodes in theory have certain definite advantages, their development was not satisfactory for practical purposes from technological, design, and manufacturing points of view. Especially this is true in the context of large scale production.

The above-mentioned drawbacks can be avoided by using the new electrode constructions according to the present invention. It was found surprisingly that channeled micromachined or etched insulator electrodes give significantly higher performance while allowing fast bioreactions to occur at the novel electrodes of this invention. The channeled electrodes described in the present invention have several advantages over the prior art.

SUMMARY OF THE INVENTION

The present invention is directed to an insulating film-coated electrode for producing electrogenerated chemical reactions in a reaction medium, the electrode comprising an electrically conductive material, which is coated with an electrically insulating film, wherein the electrode is channeled to provide a high specific surface area for the electrode. The invention also concerns insulator electrode devices containing such electrodes as working electrodes, as well as methods for their preparation and their use e.g. for decomposing of organic or inorganic molecules in an aqueous solution or for effecting electrochemically induced reactions in such solution, or for the sterilization of aqueous solutions from microbes. The various characteristics of the invention are described in the appended claims.

The device according to the invention comprises high specific surface area electrodes based on a channeled or microstructured conducting base material that has been coated with an organic or inorganic insulating film or multiple layers of such films. The said film can cover the said electrically conductive material completely or covers the material at least at the portion of the electrode which will be in contact with or immersed in the reaction medium when in use, that is the reaction inducing part of the electrode. An example of the chemical reactions performed with the said devices comprises exciting one or several label compounds into an excited state which is spontaneously de-excited by emission of ultraviolet, visible or infrared light, in aqueous solution. This provides the basis for reproducible analytical applications in bioaffinity assays such as immunoassays and DNA-probing assays.

DESCRIPTION OF THE DRAWINGS

FIG. 12. Photograph of specimen of example illustrated in FIG. 11 with working electrode (silicon thickness 525 µm) channel width 180 µm, bridge width 720 µm, SU-8 thickness 70 µm; glass thickness 525 µm and counter electrode thickness 500 µm. The counter electrode is at the top, the glass window at the bottom and the working electrode in between.

DETAILED DESCRIPTION OF THE PREFERRED EMBODIMENT

Figure 1:
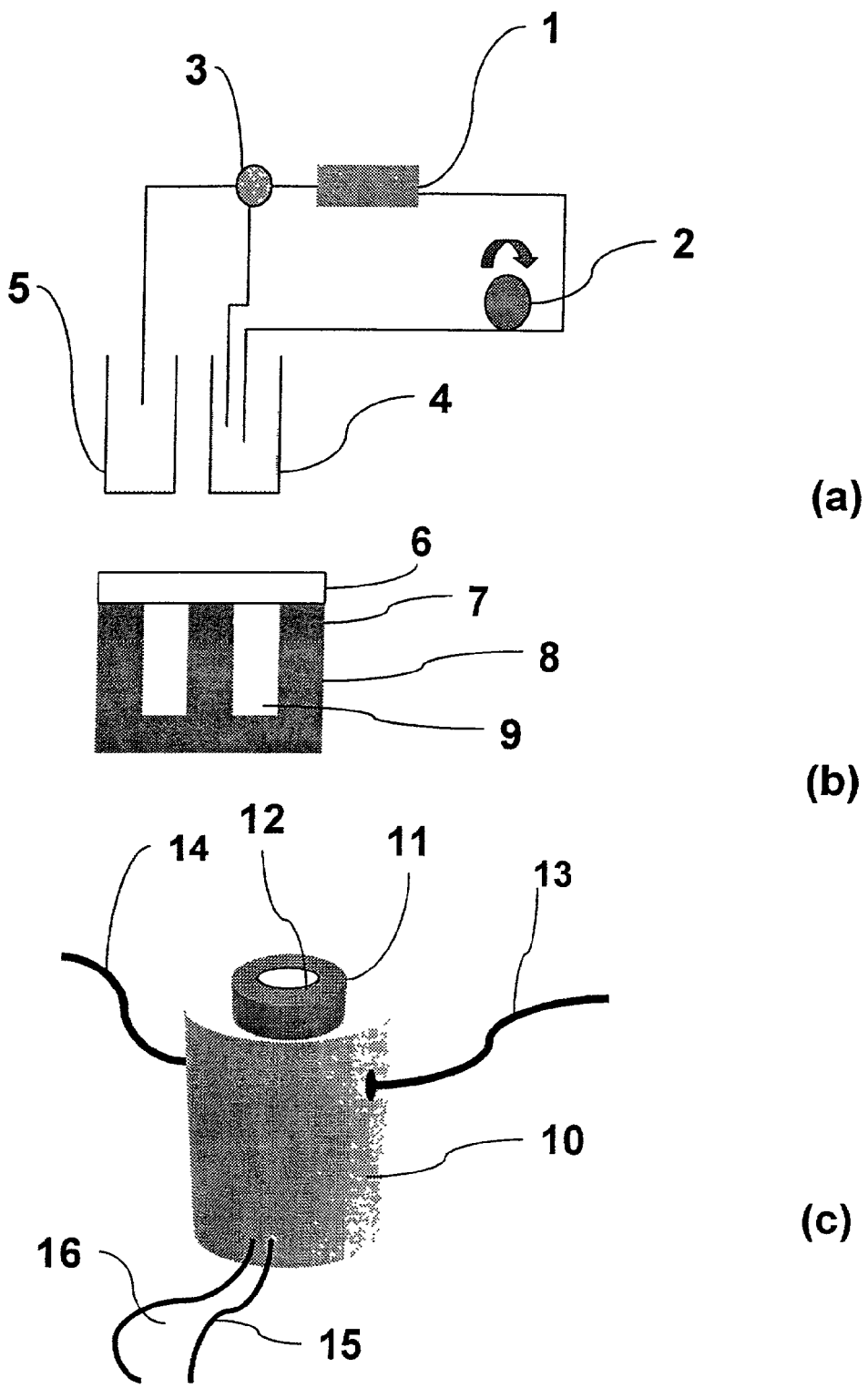
FIG. 1. (a) The figure presents a schematic measuring set-up for the use of insulator electrode devices in simple flow-through systems and circulated solution flow systems. (1) A channeled insulator electrode device, (2) peristaltic pump, (3) valve leading either to a waste chamber, (5) or circulation liquid chamber (4). (b) The figure displays a structure of a channeled insulator electrode device. The simplest device is composed of a single thin layer channel between planar thin insulating film-coated working electrode and planar metal or optically transparent counter electrode, such as ITO-coated glass electrode or conductive polymer coated plastic electrode. Normally, the working electrode has multiple small-diameter channels and the counter electrode has either a planar or a channeled structure. (6) Planar metal or optically transparent counter electrode, (7) insulator spacer (e.g. SU-8), (8) Insulating film-coated channeled working electrode. (c) A schematic diagram of a housing of flow-through insulator electrode devices which allows light detection from the device either by optical cable or by putting a photomultiplier tube window close to the flow-through device housing window. (10) Housing body, (11) Screwable housing cap to tighten the flow through device, (12) Optical window to allow light detection from the flow-through devices, (13) Inlet tubing, (14) Outlet tubing, (15) and (16) anode and cathode wires connected to a pulse generator. The contacts to the electrodes inside the housing have to be arranged differently depending on whether the working electrode chip or counter electrode is optically transparent. In the applications, in which the light detection was not needed, the optical window (12) allowed to see that no gas bubble problems etc. were occurring.

The aim of the invention is the provision of methods and devices, with which novel electrochemical reactions are generated in specially constructed micropores or channels. The advantages of the present invention are illustrated by the electrochemical reactions of different types of luminescent label compounds. Such resulting luminescence can be commercially applied, for example, to the detection step of fast bioaffinity assays. One of the basic embodiments of the invention is the use of short diffusion distances of analytes and reagents provided by the design of high-surface area electrodes and miniaturized reaction and measuring cells. Other applications of the present invention includes various chemical reactors to be used in micro or macro scale.

According to one embodiment, the invention concerns a method for electrical excitation of a label molecule, comprising at least partially immersing an insulating film-coated electrode in an electrolyte solution containing at least one label molecule; exciting said label molecule by an electrical pulse from said electrode, thereby producing an excited label; detecting luminescence emitted by said excited label; and quantifying the presence of the label based on the detected luminescence, wherein said electrode comprises an electrically conductive material and at least the portion of said electrode which is immersed in said solution is substantially covered with an electrically insulating film having a band gap equal to or greater than 5 eV; wherein the surface of the electrode is channeled to give at least a 1.5 times higher specific surface area of the electrode as compared to that of a corresponding non-channeled electrode.

The invention also concerns a flow-through electrode device comprising an insulator electrode device as defined, the electrode comprising flow channels of a diameter of 10–500 μm and channel lengths of less than 10 mm, extending from one end of the electrode to the other end, the flow-through device additionally comprising an inlet flow-distributor for a sample liquid, for distributing the liquid into the separate flow channels of the electrode, and an outlet collector of the liquid from the electrode device, the device comprising means for detecting and measuring emitted light from all channels integrally or separately from each of, or from a group of channels.

Definitions in the Context of the Present Invention i) "An electrode", according to the present invention, means a source of electric current achieved by electrodes, anode and cathode, immersed in an electrolyte solution. The electrodes deliver a pulsed electric current induced by applied voltage pulses and produce chemical reactions shown, for example, as light generated from luminescent molecules.

ii) "A thin insulating film-coated electrode", or "an insulator electrode" means an electrode as defined in WO 98/36266 (U.S. Pat. No. 6,251,690; Kulmala et al.), the contents of which is incorporated here for reference, and has a coating layer, or one of the layers, consisting of a material that has band gap larger than 5 eV. The electrically conductive material of the electrode is coated at least at those portions of the electrode which in use will be in reactive association with or immersed in the reaction medium, that is the insulating layer covers said electrically conductive material at least at the portion(s) of the electrode which are reaction inducing or activating in use. Usually the electrically conductive material of the electrode is fully coated by the insulating layer, however.

iii) "A channeled thin insulating film-coated electrode" means a thin insulating film-coated electrode made by different techniques, such as etching or micromachining to produce channeled structures or microstructures. A channeled structure can also be expressed as being a microstructure. A channeled or microstructured electrode or electrode surface thus means within the context of this invention that the electrode comprises any combination of surface microstructures, such as miniaturized channels, canals, grooves, trenches, spikes, pillars, columns or pores, which result in the surface area of the electrode being essentially increased as compared with that of the planar or non-channeled electrode as described in WO 98/36266 (Kulmala et al.) and in other literature references, and/or that the molecular diffusion distances at the electrode device are reduced due to the miniaturization of the surface structure. One embodiment for the microstructures according to the invention comprises columns or walls having a high aspect ratio, that is ratio of height to width, and arranged in rows, for example where a subsequent row being arranged off-set from a previous row of columns.

iv) "A label molecule" is a molecule, free in a solution or bound to other molecules, which can be induced to produce light by electrical pulses at the thin insulating film-coated electrodes.

v) "An insulator electrode device" means here a construction of at least a pair of electrodes (a combination of a channeled insulating film-coated working electrode and a conventional counter electrode, or a channeled insulating film-coated working electrode together with a conventional auxiliary and reference electrode), which construction is used as a generator of chemical reactions. In preferred applications and examples of this invention, light from one or more of species of electrochemiluminescent label molecules is demonstrated as a consequence of these electrochemical reactions. An insulator electrode device can also comprise a channeled or microstructured electrode as a working electrode, positioned between two current delivering electrodes in a solution and an electric field, but out of electronic contact with said electrodes.

vi) "Specific surface area" of an electrode means a surface area of electrode base material that is textured or channeled so that the surface area of the electrode is higher than the nominal facial electrode area. In such an electrode the productivity of light from a certain area is increased while the capacity of the immobilization of antibodies, antigens, oligonucleotides, and related bioaffinity substances is highly increased.

vii) The specific surface area of an electrode is considered to be high, if the effective surface area of an electrode is at least 1.5 times the nominal facial surface area of a corresponding non-channeled, planar electrode. In such an electrode the surface area has thus been increased with a factor of at least 1.5 by the provision of channels or microstructures therein, for example of that known from WO 98/36266. The channels or microstructures in the electrode are preferably dimensioned and arranged in such a way that the diffusion distances of the analytes and the reactants in the chemical reaction media to the surface is short, typically of the order of 10 nm to 1 mm, such as 1 to 500 μm, advantageously 1 or 10 μm to 100 μm, while still providing for the possibility of a flow of the medium in said structures. The electrode can thus e.g. comprise channels of a diameter of 10–500 μm and channel lengths of less than 10 mm, extending throughout the electrode, that is along the length of the electrode, from one end of the electrode to the other end.

Channeled insulator electrode devices can be exploited to accomplish divergent goals in analytical and organic chemistry:

i) the high surface area of the electrode can be used to increase the coating efficiency of the bioadsorbent (e.g. antibody, antigen, or oligonucleotide), ii) the sensitivity of the electrode/nominal square area is increased because of (i), iii) the small diffusional distances in the narrow structures of the electrode device will drastically reduce the diffusion times inside the electrode, thus providing significantly less analysis time iv) the electrode devices can be used as the working part of sensitive flow-through detector devices in flow analysis such as in flow injection analysis, in high performance liquid chromatography and in capillary electrophoresis and chromatography, v) when the detector devices are suitably constructed to form individual channels (say, 1–100 μm in diameter), their surfaces can be coated with different bioadsorbents either by physical adsorption or chemical coupling, such as with antibody, antigen, oligonucleotide which compounds can specifically bind analytes from the liquid flow. Each channel can be separately used as a detector for a specific gene or gene product in microarray technology.

vi) several unusual organic and inorganic reactions (producing light or not) can be achieved by high surface-area channeled insulating film coated electrodes.

It has been experimentally observed that extremely harsh redox conditions can be produced at thin insulating film-coated electrodes, and that these conditions closely resemble those of the radiolysis of water. Electrically induced luminescence at aluminum electrodes has already been studied for several years using electrodes with natural oxide film coverage, which yield irreproducible results, as described e.g. in references: J. Kankare et al. *Anal. Chim. Acta*, 256 (1992) 17. and *Anal.Chim. Acta*, 266 (1992) 205. The nature of the metal itself was assumed to be the most important component of the system and the importance of the naturally existing 1–2 nm thick oxide film was therefore not understood. For instance, in the literature, tantalum electrodes were claimed to be fully equivalent with aluminum electrodes and usable in the same applications as aluminum electrodes (UK Patent GB 2 217 007 B). However, tantalum oxide is an n-type semiconductor with a band gap ca. 4 eV (see e.g., S. Morrison, "Electrochemistry at Semiconductor and Oxidized Metal Electrodes", Plenum Press, New York, 1980, s. 183) and, therefore, oxide-covered tantalum electrodes cannot be used according to the principles of the present invention. In the present invention, an insulator electrode is defined as an electrode for which at least one of the coating layers consists of material that has a band gap larger than 5 eV.

The insulator electrodes preferably contain around 4 nm thick, good-quality insulating film, upon the surface of which or in the vicinity of which the bioaffinity reactions are performed, or to the vicinity of which the products of the bioaffinity reaction are brought with a suitable medium such as an electrolyte solution, or upon suitable supporting material such as the surface of magnetic latex particles. The applicability of the present invention is partially based on the fact that the existence of an insulating film enables the Fermi-level of the base conductor to reach highly cathodic pulse potentials, and subsequently allows a transfer of energetic (hot) electrons into the electrolyte solution, either by tunneling through the insulating film or as a consequence of an electron avalanche. If the Fermi level of the electron-emitting base conductor is above the conduction band edge of water (−1.3 eV on vacuum scale), the hot electrons can be injected into the conduction band of water in the small channels of the present invention and thus produce hydrated electrons as cathodic mediators for reduction reactions, as has been described in the cases of radiolysis of water or photoionisation of solutes in larger volumes in water.

The insulating film on the electrodes also provides the basis for the Fermi level of the base conductor to reach highly anodic pulse potentials, which makes a new anodic process, a hole injection into the valence band of water, possible. This process is analogous to the electron injection into the conduction band of water, and results in the generation of hydroxyl radicals by dissociation of $H_2O^+$-ion formed (valence band hole in the water) to proton and hydroxyl radical, as known from the pulse radiolysis of water. Certain metal oxides, $Al_2O_3$, $SiO_2$, and MgO, may produce hydroxyl radical also by other solid state mechanisms as described in references: S. Kulmala et al., "Cathodic Electrogenerated Chemiluminescence of Luminol at Disposable Oxide-covered Aluminum Electrodes", Anal. Chem., in press.; S. Kulmala and T. Ala-Kieme, Anal. Chim. Acta, 355 (1997) 1–5. In addition to hydroxyl radicals, sulfate and phosphate radicals can also be generated from suitable precursor molecules at thin insulating film-coated electrodes WO 98/36266 (Kulmala et al.).

According to the present invention, electrodes have a conductive base layer that can be composed of e.g., carbon (graphite, glassy carbon) or metal such as Be, Mg, Al, Ga, In, Au, Pt, Cu, Fe, Ru, stainless steel, Zn, Hg, Ag, Ni, Pd, Hf, Zr, (also Ta is suitable as the base conductor although $Ta_2O_5$ is not usable as an insulating film). However, it is possible that the electrode works better, the smaller the work function of the base conductor.

The conductor can also be a heavily doped semiconductor or metal oxide such as Si, Ge, Sn, ZnO, $SnO_2$ etc. The base conductor can also be composed of conductive polymer such as polyaniline, polypyrrole, polyacetylene, polytiophene or of corresponding polymers made from substituted monomers. The resistivity of the base conductor should be <10 $\Omega$cm.

Insulating layer(s) of the electrode can be made of some oxides, such as, $SiO_2$, MgO, CaO, SrO, BaO, $Al_2O_3$, $HfO_2$; of some other inorganic insulators, such as diamond, silicates or nitrides, some organic insulating materials such as paraffines, other solid or liquid hydrocarbons, organic insulating polymers such as, Teflon, polyethene, polypropene, polystyrene, polyacrylamides, epoxy-plastics etc. Normally, metal oxides can be used as the insulating film material only in the case of utilization of pulsed excitation, because DC-cathodisation usually ruins the insulating properties of the oxide films within a few milliseconds.

Electrical contact to the electrodes is usually obtained by metal wires from the electrical pulse source. However, any other electrically conductive material is possible or may be technically advantageous, especially at the immediate points of contact to the electrodes. In the case of high (or low) resistance of the contact material, the pulse height (voltage) is easy to adjust to obtain optimal working potentials at the electrodes. In addition to a metal, the electrical contact material can be a conducting polymer, or an electrolytic solution in liquid or gel phase. According to the present invention, electrical contact to a channeled electrode device can be obtained also by such materials. Sometimes, the electrical contact may be technically non-trivial, as described above, for example, in the context of microchip technologies. Electrical contact to cathode and anode may also differ.

Coating films of the channeled electrodes can be manufactured by chemical oxidation, anodic oxidation, by Atomic Layer Epitaxy (ALE), by spraying polymeric or polymerizable material on the surface of the electrode, by dipping the electrodes in the above-mentioned solution and letting the solvent evaporate, by Langmuir-Blodgett methods or by other methods known from other coating processes, by spin coating etc. Especially in the case of silicon, there are several alternative methods known in the electronics industry to manufacture good-quality $SiO_2$ films.

A drawback of the technology of insulating film-coated electrodes disclosed in WO 98/36266 (Kulmala et al.), was that assay times are relatively long due to the macro scale cells and low specific surface areas of the working electrodes. The diffusion distances can be shortened and analysis times can be drastically shortened, if the surface texture of the base conductor is modified to have small-dimensional grooves or pores yielding a higher specific surface area.

The channeled electrodes described have several advantages over the previous art:
i) higher sensitivity/nominal square area,
ii) directly suitable to flow-through detectors,
iii) manufacturing advantages, iv) diffusion/reaction rates are highly accelerated,
v) highly expensive and disturbance-sensitive robots are not needed
vi) extremely efficient electrochemical reactions are achieved.

The invention provides a method of manufacturing the electrode as defined, comprising providing an electrically conductive material, forming channels in and/or on said material, and providing an electrically insulating film coating on said channeled or microstructured material.

The base conductor material can be textured and channeled in various ways to give a high specific surface area prior to coating with an insulating film by mechanical micromachining treatments such as sawing or drilling, by chemical etching, electrochemical etching, dry etching, such as plasma etching or reactive ion plasma etching, moulding and so forth. The present invention makes a dramatic improvement over the prior art, especially, by increasing the speed to a level required in the analytical fields of Point of Care (POC) or High Throughput Screening (HTS). A preferable base conductor material is relatively strongly doped n- or p-type silicon channeled by above-mentioned methods.

Other preferable substrate base materials are composed of plastics. This technology includes accurate micromachining of a master specimen from, for example, silicon which is then used for propagation of (non-conductive) inexpensive plastic copies by moulding techniques. The plastic models can be covered with a thin metal coating e.g. by deposition techniques. The metal surfaces may then be covered by an insulator layer as described in the prior art. Another approach may involve fabrication of microchanneled devices from conductive plastics and covering them with organic insulators according to the methods described earlier.

Although, in principle, naturally existing oxide film-covered unchanneled aluminum electrodes can be used to excite some label substances, the commercial utilization of these electrodes is impossible due to the poor quality of the natural oxide film which results in excessively irreproducible analysis results (S. Kulmala, "Electrogenerated lanthanide(III) luminescence at oxide-covered aluminum electrodes and closely related studies", Academic dissertation, Turun yliopisto, 1995, pp. 25–31 and 114–119). However, the reproducibility of the analysis can be improved to the level required, by channeling followed by fabrication of good-quality insulating film with suitable thickness. It is characteristic for the present invention that the coating film/films are carefully layered upon the channeled base conductor, while taking care that the total thickness of the coating is optimal. In the case of aluminum, this kind of insulating film cannot be produced by letting aluminum be oxidized in room air, but can be manufactured by other sophisticated methods. Preferred methods are Atomic Layer Epitaxy (ALE) or anodic oxidation of aluminum in suitable electrolyte solution and successive coating with organic material(s) to prevent the aqueous solution spoiling the insulating properties of the oxide film during the bioaffinity assays. This spoiling is always inevitable to some degree in the absence of other shielding coating layers. Aluminum films can also be made by coating some other channeled material with aluminum, such as plastic, graphite, glassy carbon, metal, and subsequently oxidizing aluminum and adding a final shielding layer.

Suitable polymeric films for coating of oxide films can be readily created by spin coating or dipping the electrode in polystyrene solution which has been made by dissolving polystyrene in an organic solvent such as benzene or toluene. In an analogous way, many other polymers that can be dissolved as dilute solutions of solvents can also be utilized in the fabrication of thin polymer films. Polymeric films can also be made from mixtures of polymers or they can be doped with inorganic materials. Polymeric films can be made exceptionally smooth by using a commercially available apparatus for growth of these films. The electrode surface need not to be totally coated with an insulating film designed for active use in excitation of labels, but insulating films can be in the form of very small spots or islands, surrounded by a thicker insulating film which does not allow current transport by any mechanism.

Analogous polymeric films can also be created by allowing polymerization to occur at the surface of a channeled conductor or at the surface of a channeled insulating film-coated conductor. In this case, the reactants of the polymerization reaction are dissolved separately in a suitable inert solvent such as toluene, benzene, dichlormethane, etc. One of the components can be deposited with a special micromachined deposition device, or the electrode is automatically dipped in a solution of the component and solvent is allowed to evaporate or the liquids are pumped through the channels. Another component can be deposited in an analogous way and polymerization is allowed to occur. Alternatively, the reactants of the polymerization reaction are mixed in a solvent just before deposition. In all cases, the optimal thickness of the films can be experimentally found by adjusting the concentration of coating materials in the solvents or by using coating apparatus for adjustment of the film thickness. In some cases it is preferable to coat electrodes by spraying. The polymer must be divided in the spray into droplets with diameter 1–1000 nm in an appropriate solvent, such as, toluene, benzene, cyclohexane, chlorinated hydrocarbons, DMF, DMSO, or alcohols.

$Al_2O_3$, MgO and other alkaline earth metal oxide coatings are less studied than the rather well known $SiO_2$ films. $SiO_2$ is the most important insulating film material in the electronics industry based on silicon technologies. There are several methods available for fabrication of good-quality $SiO_2$ films in this field of industry.

Inorganic insulating films can be totally replaced with suitable organic insulating films, if the production of the oxidizing species, generally necessary for excitation of most of the label substances, is provided by addition of suitable coreactants such as peroxydisulfate, peroxydiphosphate, or hydrogen peroxide which produce strongly oxidizing radicals via one-electron reduction. Often, a combination of inorganic and organic film is preferable.

A high electric field across the insulating films also induces solid state electroluminescence in the film, to some extent. This solid state electroluminescence also facilitates the excitation of luminophores by energy transfer from the intrinsic emission centers, if the luminophores are located sufficiently close to the insulating film. This effect enhances the proximity effect required by homogeneous assays.

The insulating film-coated working electrode can be either optically transparent or non-transparent depending on the optical properties and the thickness of the conducting material. Usually the transmittance of the sufficiently thin base conductor is high enough in the desired optical range. The use of a transparent working electrode makes possible the measurement of electrically excited luminescence through the working electrode and the electrode surface texture can be so designed that the light can be optically coupled into the transparent substrate matrix and guided to light detector/detectors by the principles of modern optical wave guides.

The selection of the counter electrode used in the method is not so critical as the working electrode. This allows the freedom to make extremely complicated 3-dimensional structures of the electrode device. The basic demand for the design of the counter electrode is that its current distribution function for even light production from the working electrode is optimal. Because its construction is not always critical for the performance of the electrode device, the design of the counter electrodes can be modified to improve other functions of the electrode device, such as flow properties and diffusion distances, which are equally important for the practical function of the insulator electrode device. Conventional inert counter electrode materials are well suited, and even certain metals which are anodically dissolved can be used, because the measurements usually are made in the time scale where the anodic products from the counter or auxiliary electrode do not have time to diffuse to the working electrode. Also some metal oxide electrodes, such as indium tin oxide, are well suited as an anode material. In this case the anode material can readily be made optically transparent. Stainless steel is also an advantageous electrode material. If a non-transparent metal electrode serves as a counter electrode its shape can be chosen so that the luminescence is measurable behind the counter electrode. For instance, a wire electrode covering only a very small part of the surface of the working electrode can be used or hole(s) can be drilled through the anode material to allow the light detection from behind the anode. An optically transparent counter electrode can be prepared from adequate metal film or deposited microgrid, e.g., from plastic or glass coated with a thin Au film which can be further coated with a thin shielding film allowing electron and/or hole tunneling through the outer film.

If the thickness of the insulating film on the working electrode is suitable, the excitation of the label in the detection stage can be done by cathodic voltage pulse train, but in the case of the base material being anodically oxidizable material such as Si, Al, Be or Mg, it is sometimes beneficial to grow the oxide film thicker using an oxidizing anodic pulse before each cathodic excitation pulse.

The electrode devices of the present invention can be manufactured after primary photolithography steps by combining different materials such as silicon with glass or quartz by anodic or other bonding steps, followed by etching and/or micromachining steps, further followed by metallization steps using methods such as sputtering or electroplating. The electrode device can be formed from a single chip wherein the anode/anodes and cathode/cathodes are integrated or by combination of separate anode and cathode chips. The electrode device can have resist films or polymeric films such as PDMS or SU-8 as a vital part of its functionality.

The novel channeled insulator electrode devices described in the present invention can be used to perform a large spectrum of unique and efficient chemical reactions in micro or macro scale. Such reactions can produce or not produce light. Macro scale devices can be exemplified by reactors of organic chemistry, sterilization equipments of water, and electrochemical decomposition of harmful pollutants. In micro scale, the preferred applications include micro reactors and electrical excitation of various kinds of luminophores as presented in the description and Examples of the present invention. It is obvious that also many other kind of molecules can be excited at insulating film-coated electrodes with the present methods. The use of channeled insulating film-coated electrodes having high specific surface area is not limited to certain equipment constructions or analytical methods described hereby and also the optimal design may differ slightly according to the exact applications.

EXAMPLE 1

Decomposition of Benzene within Channeled Insulator Electrode Device

Preparation of planar silicon pieces. Planar p-Si disc crystal type (100) (resistivity 10–20 mΩ cm) was placed on a plastic support and cut into 20 mm×4 mm pieces using a saw. Finally the disc was rinsed with distilled water and then stored for later use.

Preparation of grooved silicon pieces. Before sawing grooves, p-Si disc was placed on a plastic support for cutting. Grooves (width 30 $\mu$m, depth 400 $\mu$m) at 60 $\mu$m intervals and grooves (width 200 $\mu$m, depth 400 $\mu$m) at 400 $\mu$m intervals were cut into a silicon wafer. After that the disc was cut to 20-mm length pieces of variable width for easier handling while cleaning. The plastic support used for cutting was removed by immersion in acetone. The disc pieces were immersed in RCA solution ($H_2O:NH_3:H_2O_2$-5:1:1) at 80° C. for 30 minutes followed by rinsing in distilled water. This was done to remove the excess silicon powder and other impurities from the surface of the wafer. The silicon wafer pieces were then etched isotropically to smoothen the cut surfaces of the wafer. A solution of 3% HF, 77% $HNO_3$, and 22% $CH_3COOH$ was used. The wafer pieces were immersed in this solution for 10 s to remove the top layer of silicon from the wafer surface. After rinsing with distilled water the wafer pieces were dried with nitrogen gas. In order to complete the cutting of the etched disc pieces into 20 mm×4 mm dimensions without making them dirty again in the cutting process, the disc pieces were coated with a thin film of positive photoresist, and then allowed to dry in oven at 80° C. The coated disc pieces were then cut into 20 mm×4 mm dimensions. The plastic support, used for cutting, as well as the photoresist were removed by immersion in acetone. The 20 mm×4 mm pieces were additionally rinsed twice more in pure acetone, followed by cleaning in isopropanol, and finally rinsed three times in distilled water.

Figure 2:
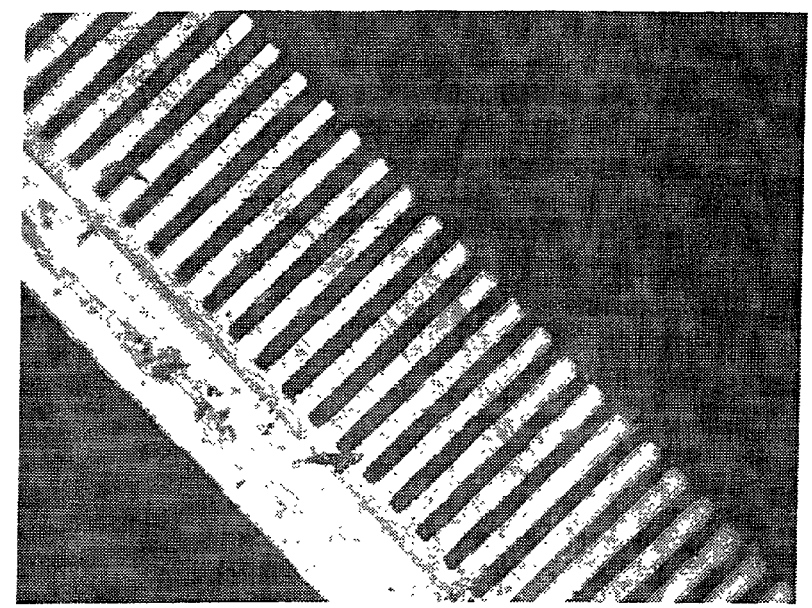
FIG. 2. (a) a p-type Si-electrode grooved by sawing with 20 $\mu$m wide blade. (b) The bottom of a groove of the electrodes polished by isotropic etching as monitored by scanning electron microscope.
Figure 2:
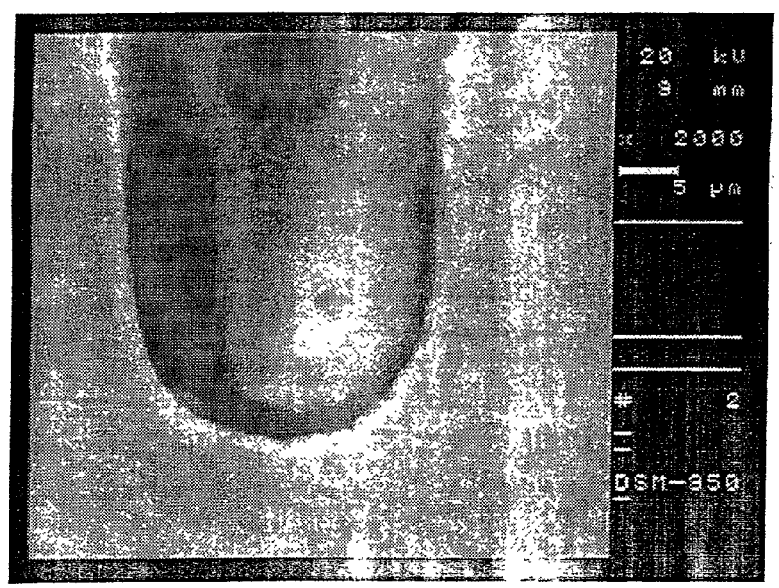

FIG. 2. (a) displays a p-type Si-electrode grooved by sawing with 20 $\mu$m wide blade. The sides and the bottom of the grooves polished by isotropic etching were relatively smooth and round as displayed by SEM picture in FIG. 2 (b).

Thermal oxidation of silicon electrodes. Planar silicon pieces were washed with isopropanol for 5 min, with 5% HF for 15 s, and rinsed with water. After that, the pieces were kept at 800° C. for 5 min. Silicon pieces with 30 $\mu$m grooves were washed with acetone in ultrasound bath for 1 min, with isopropanol for 5 min, with 5% HF for 15 s, and rinsed with water. After that pieces were kept at 745° C. for 7 min. Silicon pieces with 200 $\mu$m grooves were washed with acetone in ultrasound bath for 1 min, with isopropanol for 5 min, with 5% HF for 15 s, and rinsed with water. Finally the pieces were kept at 780° C. for 7 min.

Figure 3:
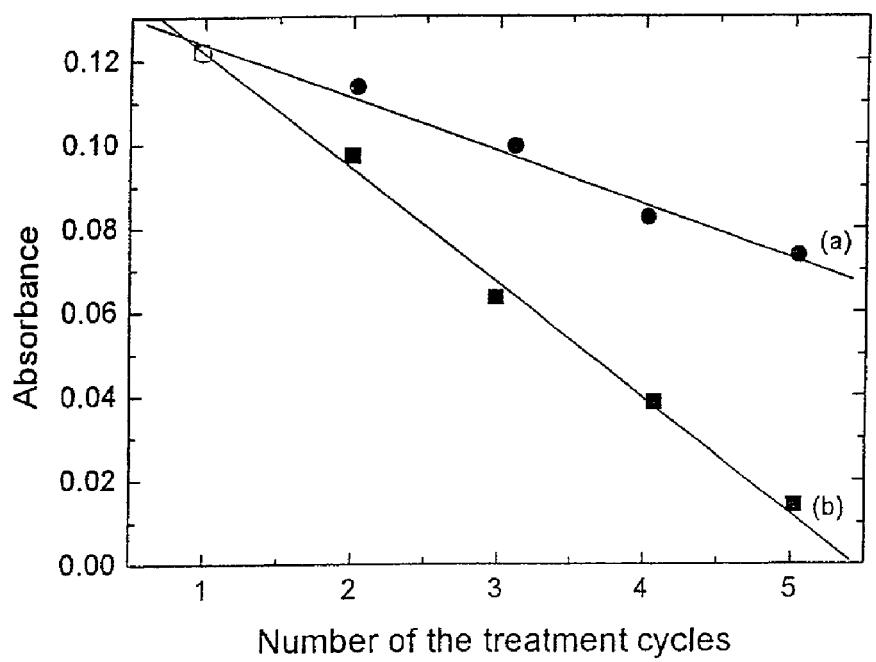
FIG. 3. Decomposition of benzene in an insulator electrode device. The decay of benzene is monitored by absorbance at wavelength of 261 nm. Curve (a) displays the results obtained with a planar working electrode (single-channel device) and curve (b) those obtained with an electrode having 30 µm wide and 400 µm deep grooves (multichannel device).

Decomposition of benzene. A saturated solution of benzene in 0.05 M sodium tetraborate buffer (pH 9.2) with volume of 1.5 ml was circulated by a peristaltic pump through the device of FIG. 1 (b) in which, the working electrode was either planar or grooved oxide-coated silicon electrode and the counter electrode was a Pt-sheet. During the circulation of the solution 100 $\mu$C cathodic pulses were applied with voltage of −30 V for 5 minute periods, after which a spectrophotometer was used to monitor the concentration of benzene by measuring the absorbance at 261 nm. Thereafter, the solution was fed back to a solution reservoir and treatments were repeated 4 times. The disintegration of benzene is displayed in FIG. 3. Curve (a) displays the results obtained with a planar working electrode (single-channel device) and curve (b) those obtained with an electrode having 30 μm wide and 400 μm deep grooves (multi-channel device).

EXAMPLE 2

Figure 4:
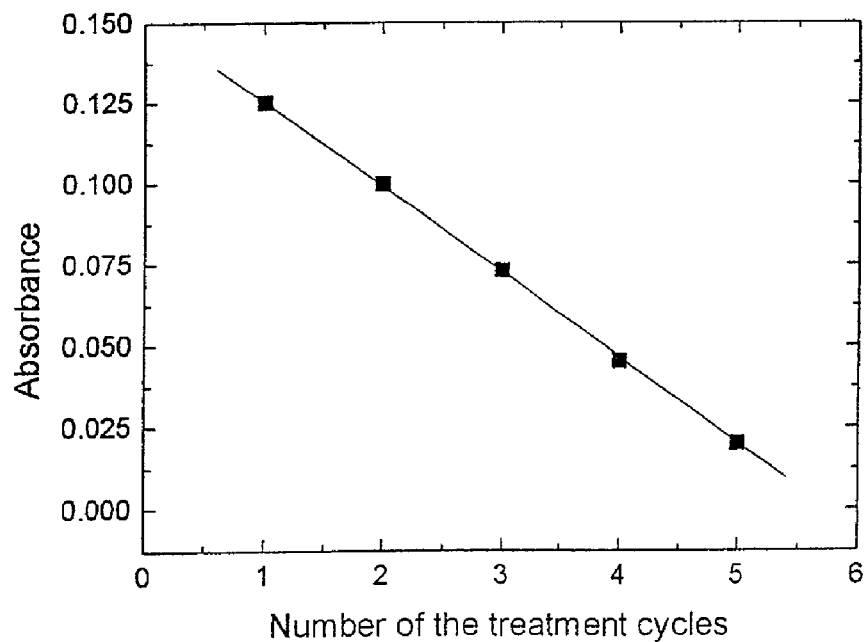
FIG. 4. Decomposition of peroxydisulfate in an insulator electrode device. The decay of peroxydisulfate is monitored by absorbance at wavelength of 224 nm.

Decomposition of Peroxodisulfate Ion in a Channeled Insulator Electrode Device Peroxodisulfate and hydrogen peroxide are very strong oxidants used in the industry e.g. in bleaching of paper pulp mass. Waste water exposed to the environment should not contain these oxidants which by one-electron reduction can produce sulfate or hydroxyl radicals which are able to induce a rupture of DNA. 1 mM solution of potassium peroxodisulfate in 0.05 M sodium tetraborate buffer (pH 9.2) with volume of 1.5 ml were circulated by a peristaltic pump through the device of FIG. 1(b) while 100 μC cathodic pulses were applied with pulse voltage of −30 V for 2-minute periods, after which the absorbance at 224 nm was measured to monitor to the concentration of peroxodisulfate by a spectrophotometer. After this, the treatment was repeated 4 times. The disintegration of peroxydisulfate in the multi-channel insulator electrode device (groove width 30 μm, depth 400 μm) is shown in FIG. 4. The results obtained with planar working electrodes showed about half of the disintegration rate observed at the present grooved electrodes (not shown in the FIG. 4).

EXAMPLE 3

Disinfection of Bacteria-contaminated Water

Grooved Si-electrodes coated with thin insulating $SiO_2$-film were fabricated as in Example 1.

Figure 5:
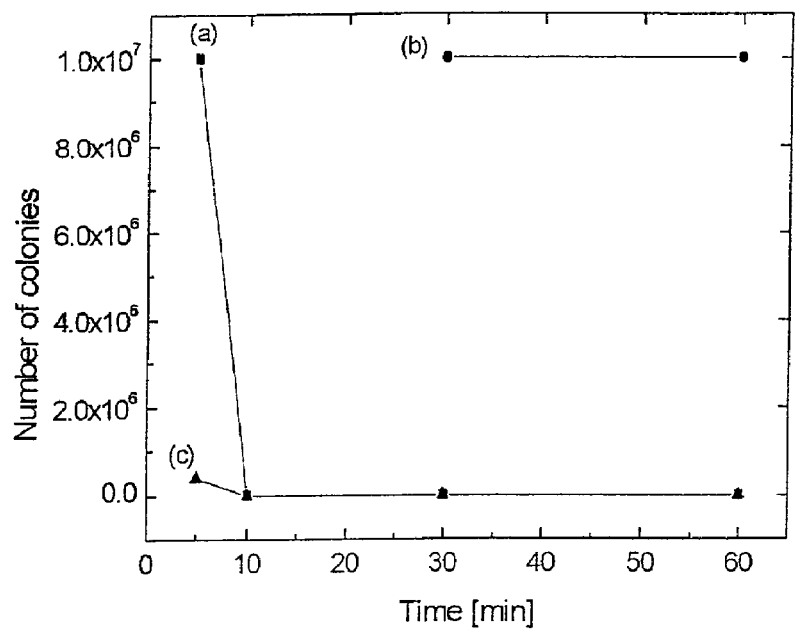
FIG. 5. Disinfection of bacteria-contaminated water. (a) Planar Si electrode, (b) planar Pt and (c) grooved Si.

*Escherichia coli* strain XL-1 was cultured in liquid LB medium at 37° C. overnight. The antibacterial effect of hot electrons were tested in a cell composed of teflon cylinder (diameter 10 mm, height 20 mm) with grooved silicon electrode bottom (cathode) and a washer made of silicone rubber. A sample of the cultured medium (500 μL) was transferred into the cell. The anode composed of vertical platinum wire was adjusted so that the tip was about 2 mm from the bottom. Bacteria were treated with hot electrons for different times (5, 10, 30 and 60 min) The hot electrons were produced with coulostatic pulse generator (charge 100 μC, voltage −40 V and frequency of 40 Hz). A cell with platinum electrodes as cathode and anode (Pt/Pt) was used as a control (treatment times 30 and 60 min). After the treatment a sample of cultured medium was transferred onto LB agar plates. After incubation at 37° C. overnight the number of the colonies were counted. FIG. 5 shows that the effect of hot electrons created by planar oxide-coated silicon electrode on bacteria is toxic (curve a) and it differs from the effect (b) of the planar Pt-electrode used. Curve (c) shows that the lethal effect on bacteria was highest in the case of channeled thin insulating film-coated working electrode. Pure standing of cultured medium in the teflon cylinder cell with silicon bottom for 60 min did not have any effect on the count of the bacterium colonies.

EXAMPLE 4

Electrochemical Synthesis in a Channeled Insulator Electrode Device

Figure 6:
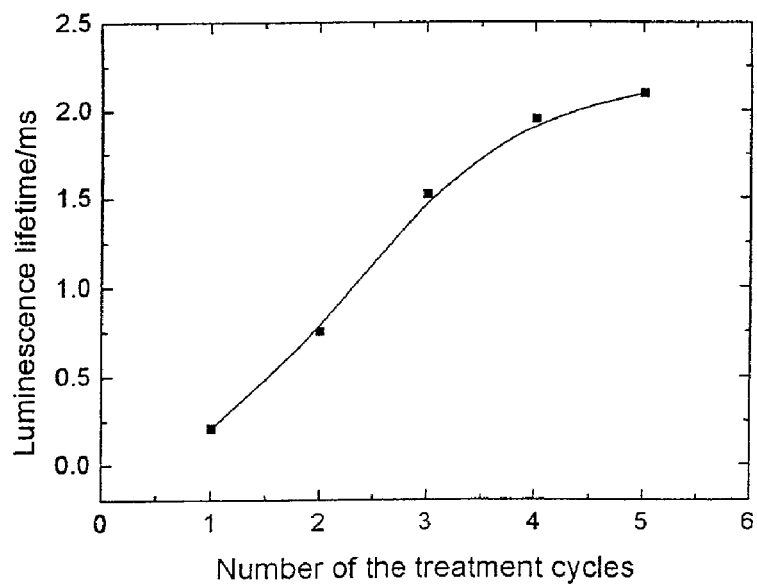
FIG. 6. Electrochemical synthesis in a channeled insulator electrode device. The change of molecular structure is monitored by luminescence lifetime measurements using excitation wavelength of 300 nm and emission wavelength of 545 nm.

A solution containing 5 μM solution of Terbium(III)-{2,6-bis[N,N-bis(carboxymethyl)aminomethyl]-4-benzoylphenol} chelate in 0.05 M sodium tetraborate buffer (pH 9.2) with volume of 1.5 ml was circulated by a peristaltic pump through the device shown in FIG. 1 (b) while 100 μC cathodic pulses were applied with pulse voltage of −30 V for 5 minutes periods. After that the time-resolved photoluminence lifetime, induced by 300 nm excitation light at emission wavelength of 545 nm, was measured by a Perkin-Elmer LS-5 spectrofluorometer. Subsequently, the treatment cycle was repeated 4 times. FIG. 6 shows that a drastic increase of photoluminescence lifetime occurs during the treatment in the channeled insulator electrode device which indicates that the molecular structure of the compound is drastically changed, e.g. polymeric form of the compound has been created. Spectrophotometric measurements suggested the that carbonyl group has disappeared from the compound.

EXAMPLE 5

Comparison of Light Production Efficiency of Labels at Planar and Channeled Insulator Electrode Planar and grooved silicon electrodes were fabricated as in Example 1.

Figure 7:
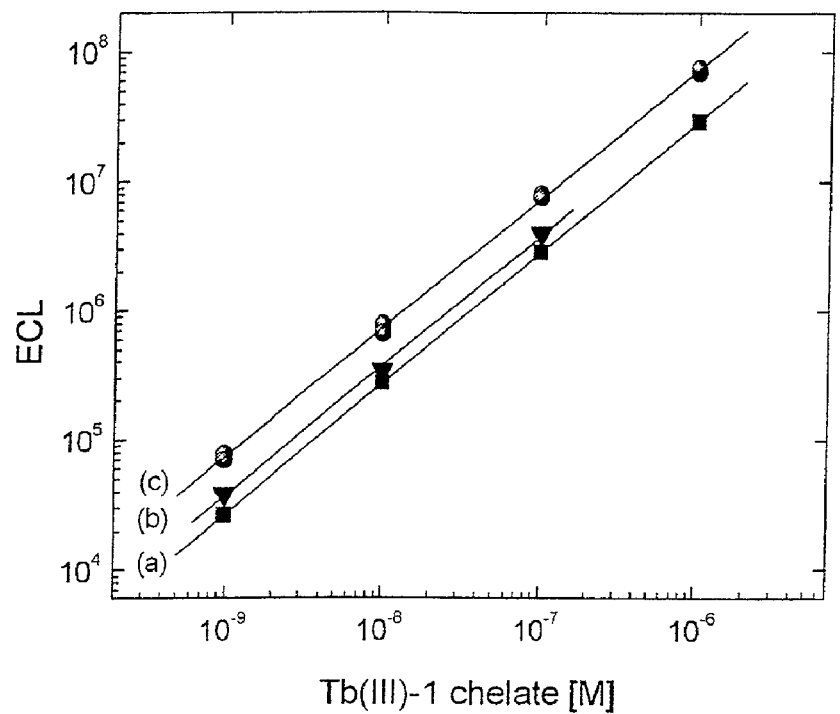
FIG. 7. Comparison of light production efficiency of labels at planar and channeled insulator electrode. The figure shows that the electrochemiluminescence is higher with grooved electrodes: (a) planar electrodes, (b) grooved (200 µm wide) (c) grooved (30 µm wide) than with planar electrodes. Tb(III)-1-chelate solution was used in the measurements.

Electrochemiluminescence measurements. ECL was measured in the measuring buffer (0.05 M borate buffer, pH 7.8, 0.1% $NaN_3$) containing different amounts of Terbium(III)-1 chelate (Tb(III) chelated by 2,2',2'',2'''-{[4-benzoyl(1-hydroxybenzene)2,6-diyl]bis(methylenenitrilo)}-tetrakis(acetate). Measuring buffer for silicon pieces with grooves of 30 μm width contained also 0.2 M $K_2SO_4$. ECL measurements were performed using an electroluminometer constructed by modifying Wallac's Arcus fluorometer (Wallac Oy, Turku, Finland). In the measurement the cathodic pulse time was 0.24 ms (−10 V) with the frequency of 200 Hz, delay time and gate time were 0.16 ms, and 1.5 ms, respectively. The intensity of ECL was integrated during 200 pulses. Different silicon electrodes served as cathodes and Pt wire was anode. FIG. 7 shows that the electrocherniluminescence is significantly higher with grooved electrodes (b=200 μm wide, c=30 μm wide) than with planar ones (a).

EXAMPLE 6

Comparison of Light Production Efficiency of Surface-bound Labels at Planar and Channeled Insulator Electrodes Preparation of planar and grooved silicon pieces. Preparation of planar and grooved silicon pieces as well as the thermal oxidation were carried out in the same way as in Example 1.

Preparation of labeled bovine serum albumin. BSA (Intergen Inc, number 3220-05) was labeled with an isothiocyanate derivative of Tb(III)-1 chelate by allowing the BSA to react with chelate in the molar ratio of 1:60 at pH 9.5. Labeled BSA was separated from unreacted chelate by gel filtration using Tris-buffer (50 mM TRIS-HCl, pH 7.8, containing 9 g/l NaCl and 0.5 g/l $NaN_3$) as the eluent. Coating of silicon electrodes with labeled and unlabeled BSA. The electrodes were coated with labeled and unlabeled BSA by incubating them for 2 hours in Tris buffer containing 68.6 µg/mL of unlabeled BSA and 0.57 µg/mL of labeled BSA. Labeled BSA was diluted with unlabeled BSA in order to get the signal into the appropriate range. Coating volume was 250 µL/well.

Washing of the coated silicon electrodes. The electrodes were washed 6 times while shaking with 300 µL of washing solution (50 mmol/L Tris-HCl, pH 7.8, containing 0.9% NaCl and 0.02% Tween 20).

Figure 8:
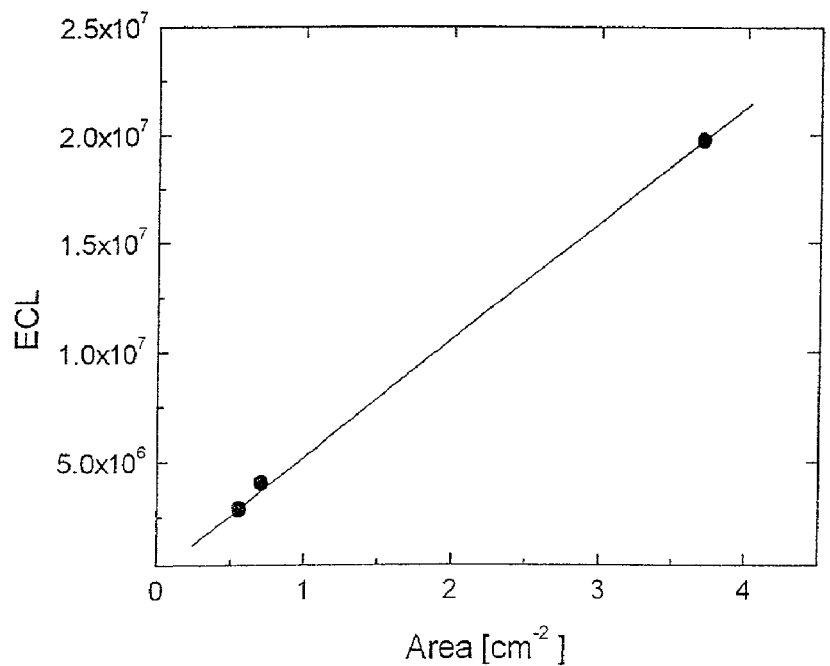
FIG. 8. Comparison of light production efficiency of surface-bound labels at planar and channeled insulator electrode. The results show that the ECL is increasing as the surface area of the silicon electrode is increasing due to the channeled structure (first point planar, the other points grooved electrodes). Electrodes were coated with Tb(III)-1-labeled bovine serum albumin.

Measurement of ECL. ECL was measured as in Example 5 except that the measurements were done in measuring buffer without addition of the Tb(III)-1 chelate. The intensity of ECL was multiplied by the ratio of unlabeled BSA and Tb(III)-1-chelate-labeled BSA. FIG. 8 shows that ECL is increasing when the degree of grooving is increasing.

EXAMPLE 7

Immunochemical Determination of C-reactive Protein at Planar and Grooved (width 30 µm, Depth 400 µm) Silicon Electrodes as Carried out in the Wells of Microtiter Strips Showing Faster Reaction at Grooved Electrodes Preparation of planar and grooved silicon pieces as well as the thermal oxidation were carried out in the same way as in Example 1.

Coating the electrodes with antibody. The electrodes were coated with mouse anti-human CRP antibody (Medix Biochemica, Finland, clone 6405) by incubating them overnight in Tris buffer containing 6.5 µg/mL of antibody. Coating volume was 250 µL/well. After this, the electrodes were equilibrated overnight in saturation solution (300 µL/well, Tris buffer containing per liter 1 g bovine serum albumin, 60 g sorbitol and 1 mmol CaCl$_2$).

Preparation of labeled antibody. Mouse antibody to human CRP (Medix Biochemica, Finland, clone 6404) was labeled with the isothiocyanate derivative of Tb(III)-1 chelate by allowing the antibody to react with chelate in the molar ratio of 1:70 at pH 9.5 overnight. The labeled antibody was separated from unreacted chelate by gel filtration.

Preparation of standards. Standards (0, 10, 100, 300 ng/mL) were made by dissolving stock solution of CRP (Scripps Laboratories, San Diego, USA) in TRIS-HCl buffer containing 0.5% BSA and 1 mmol/L of CaCl$_2$.

Figure 9:
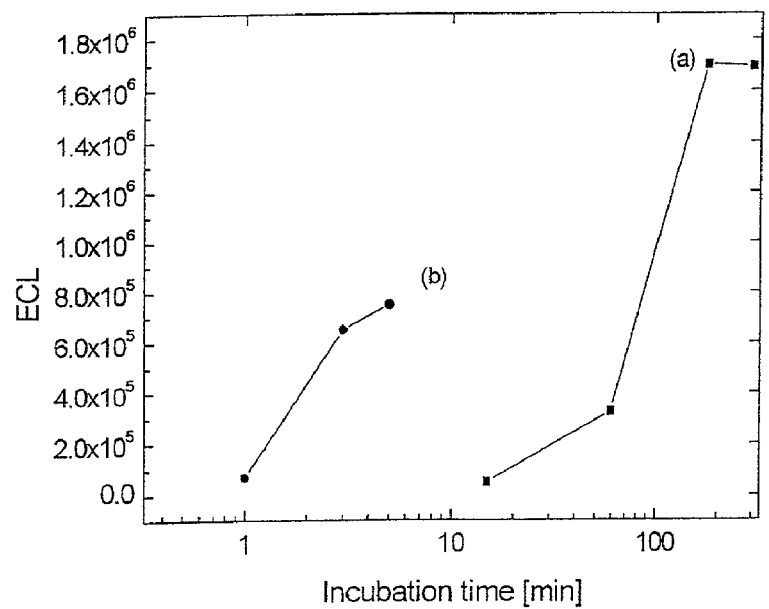
FIG. 9. Immunochemical analysis of C-reactive protein at (a) planar, and (b) grooved (width 30 µm depth 400 µm) silicon electrodes as carried out in the wells of microtiter strips. The figure shows faster reaction at the grooved electrodes.

Immunochemical detection. 100 µL of standard and 100 µL (500 ng) of labeled antibody (in the Tris-HCl buffer, pH 7.8, containing 0.5% BSA, 1 mmol/L of CaCl$_2$, 0.05% bovine-gamma-globulin and 0.01% Tween 20) were added into the microtiter wells and incubated for 1, 3, 5, 15, 60, 180 or 300 min. After incubation the electrodes were washed and ECL measured in the same way as in Example 6. FIG. 9 shows that the equilibrium of immunoreaction was reached much faster with grooved electrodes (30 µm) than with planar ones.

EXAMPLE 8

Immunochemical Equilibrium is Attained Faster in a Multichanneled Insulator Electrode Device than in a Single-channeled Insulator Electrode Device A special cell housing (FIG. 1c) was constructed to carry out the immunochemical assay of $\beta_2$-microglobulin kinetically using both planar and grooved (width 30 µm) silicon electrodes. ECL was measured in the same way as in Example 6. Preparation of planar and grooved silicon electrodes as well as the thermal oxidation were carried out in the same way as in Example 1.

Coating of the electrodes. The electrodes were coated with mouse anti-human $\beta_2$-microglobulin antibody (clone 6G12, Labmaster Ltd., Turku, Finland) by incubating them overnight in TRIS-HCl buffer containing 100 µg/mL of antibody. Coating volume was 1 mL/vial. After this the electrodes were equilibrated overnight in saturation solution (TRIS buffer containing per liter, 1 g bovine serum albumin and 60 g sorbitol). Saturating volume was 1 mL/vial.

Preparation of labeled antibody. Mouse anti-human $\beta_2$-mcroglobulin (clone 1F10, Labmaster Ltd., Turku, Finland) was labeled with an isothiocyanate derivative of Tb(III)-1 chelate by allowing the antibody to react with the chelate in the molar ratio of 1:60 at pH 9.5. The labeled antibody was separated from unreacted chelate by gel filtration.

Preparation of standards. Standards (0,10, 30, 100, 300, 700 ng/mL) were made by dissolving a stock solution of $\beta_2$-microglobulin (Labmaster Ltd., Turku) in Tris buffer, pH 7.8, containing 0.5% BSA and 0.01% Tween 20.

Figure 10:
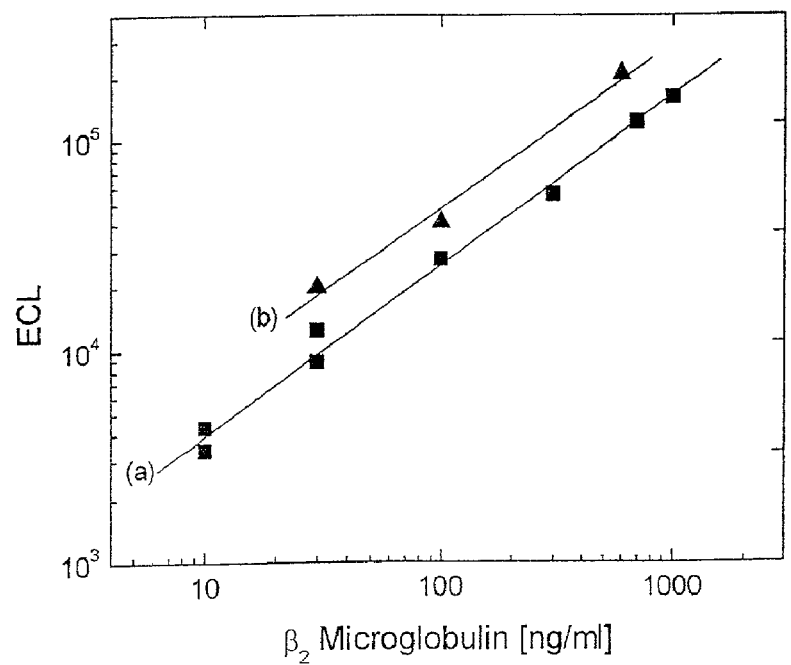
FIG. 10. Immunochemical equilibrium is attained faster in a multi-channeled insulator electrode device than in a single-channeled insulator electrode device. The figure shows that more light is received from multi-channel grooved electrodes (b) than from planar electrodes (a). A flow-through cell was used and $\beta_2$-microglobulin was the analyte.

Immunochemical detection. 100 µL of standard and 400 µL (740 ng) of labeled antibody in the Tris buffer, pH 7.8, containing 0.5% BSA and 0,01% Tween 20 were mixed in a test vial. After 15 min, 50 µL of this mixed solution was injected to the flow cell by an injector. 0.05 mol/L Tris-HCl buffer, pH 7.8, containing 0.9% NaCl and 0.05% NaN$_3$ was used as the mobile phase (flow speed 5 mL/h). After 8.7 min, the cell was washed by washing solution (flow speed 60 mL/h, 5.3 min) and measured in the same way as in Example 2. FIG. 10 shows that more ECL is generated by grooved electrodes (b) than by planar ones (a).

EXAMPLE 9

Channeled Insulator Electrode Device Containing Separately Manufactured Cathode and Anode Chip and Immunoassays of $\beta_2$-microglobulin Manufacture of Optically Transparent Cathode Chips by Bonding Glass on Si-wafer which is Subsequently Coated with SU-8 Resist Layer and Grooved by Sawing.

Fabrication Protocol of the Chip

1. Glass wafer (525 µm thick) and n-type or p-type (100, 111, or 110) 525 µm thick silicon wafer (0.01–0.02 Ωcm) were anodically bonded together, the polished side of the silicon wafer being bonded to the glass, but double-side polished wafers are preferably used.
2. Fingerprints were removed from the surface of the structure using isopropanol. Organic surface contaminants were removed by cleaning in RCA (H$_2$0: 31% H$_2$O$_2$: 25% NH$_4$OH, 5:1:1) at 80° C. for 20 minutes.
3. Structure was then dried for 2 hours in an oven at 120° C.
4. Plastic support was used to cover the glass underneath. This was done to prevent any SU-8 from covering the glass during its application.
5. 5 ml of SM 1070, SU-8 based photoepoxy was applied to the surface of the unpolished side of the silicon. The silicon wafer was spun at a rate of 500 rpm for 25 s to yield a coating of approx. 70 µm SU-8 on the silicon surface. Thickness was measured using a micrometer.
6. The solvents in the SU-8 were removed and the resist somewhat hardened by incubation of the entire structure at 90° C. for 30 mins.
7. Plastic support was removed manually from the glass.

Figure 11:
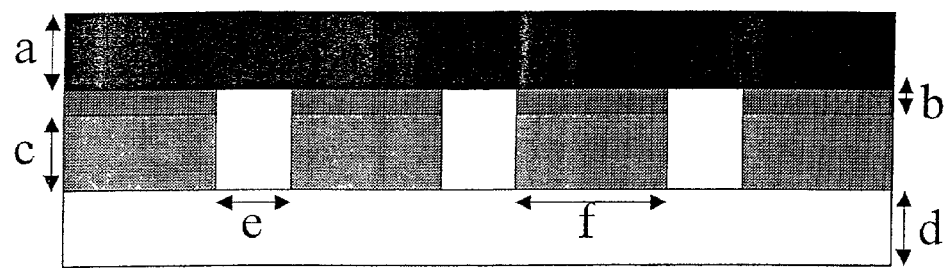
FIG. 11. A schematic side view of a 2-electrode cell formed.
Figure 12:
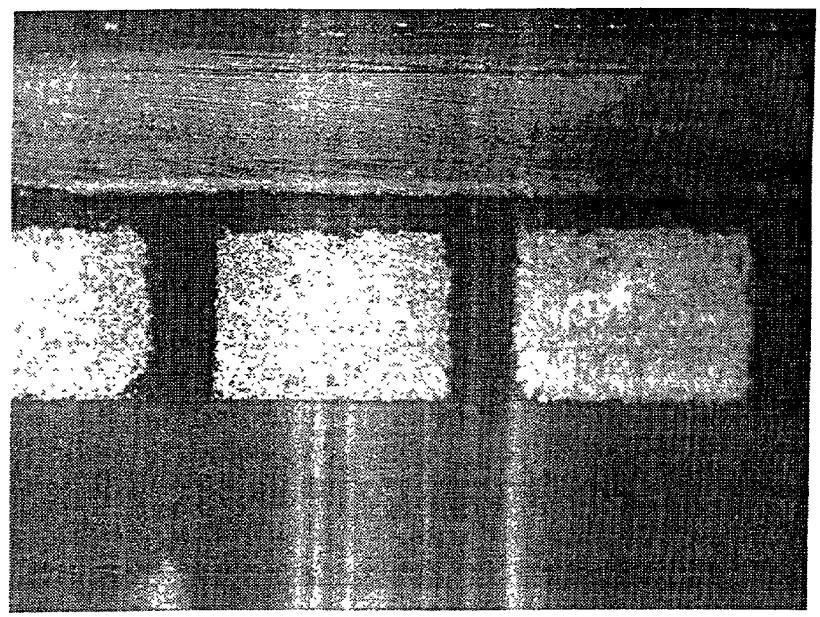
Figure 13:
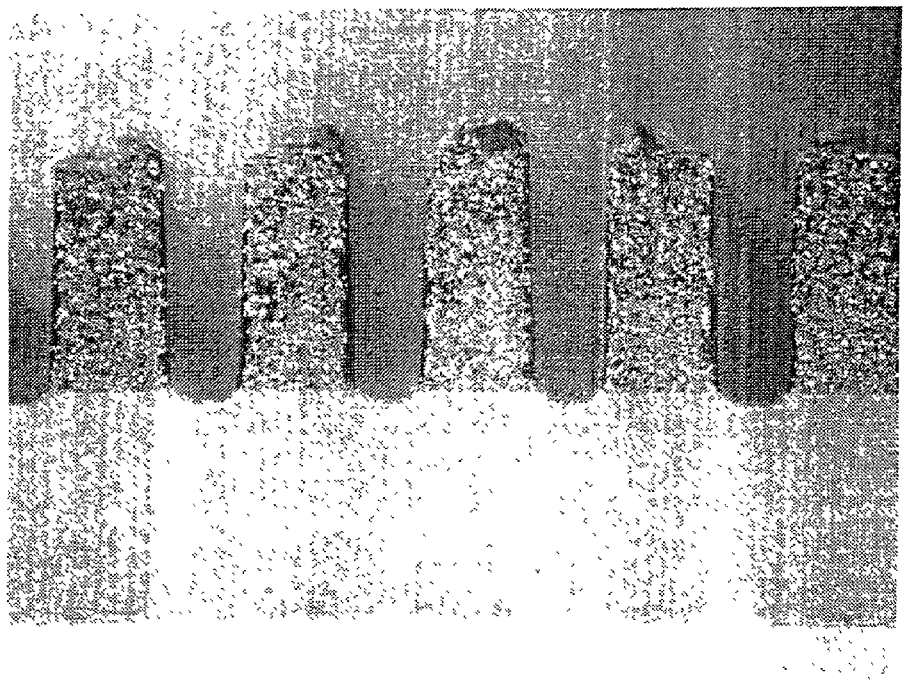
FIG. 13. Photograph of specimen of example illustrated in FIG. 11 with channel width 180 µm, bridge width 220 µm, SU-8 thickness 60 µm, silicon thickness 525 µm and glass thickness 525 µm. In this photographed batch the SU-8 layer was too soft for blade cutting at high speed. The counter electrode is not attached on top of the SU-8 layer in this case, the glass layer is again at the bottom.

8. Grooves were cut into the SU-8 and silicon using a Loadpoint Microace 3, series 3 saw and 150 $\mu$m wide blade (note 20 $\mu$m blade not strong enough to cut glass). Spindle rotation speed was 15 rpm and cutting speed was 3 mm/s. Cutting steps of 900 $\mu$m were used to allow sufficient surface interaction between the glass and remaining silicon and maintain the anodic bonding. In subsequent samples, cutting steps of 400 $\mu$m were sufficient (see FIG. 13).
9. Sawing was carried out such that the base of the grooves formed were approx. 50 $\mu$m deep into the glass, i.e. the blade cut entirely through the SU-8 and silicon.
10. After formation of the grooves, the entire structure including the glass, SU-8 and silicon was cut e.g. to 20 mm×4 mm dimensions.
11. The optically transparent cathode chip can now be integrated to the different types of measuring cells.
12. Optionally, a counter electrode of equivalent size (section of silicon in photo) was then joined to the 20 mm×4 mm structures, via the SU-8, by moderate heating. This resulted in the formation of channels as seen from the FIGS. 11, 12 and 13.

SU-8 acts as an insulator between the working and counter electrodes. It also serves to join the counter electrode to the remainder of the cell.

Analogous channeled structures in the silicon produced by sawing were also fabricated by wet etching when double-side-polished (110) wafers were used as a source of working electrodes.

Fabrication Protocol.
1. Substrate: (110) silicon wafers, 0.01–0.02 $\Omega$cm, 525 $\mu$m thick, double side polished.
2. Wafers were cleaned in RCA1 ($H_2O$: 31% $H_2O_2$: 25% $NH_4OH$, 5:1:1) at 80° C. for 10 minutes, RCA2 ($H_2O$: 31% $H_2O_2$: 37% HCl, 5:1:1) at 80° C. for 15 minutes and dipped in HF for 30 seconds before drying in $N_2$.
3. Wafers were wet oxidised for 2 hours at 1000° C. Resultant oxide thickness was approximately 350 $\mu$m as measured with an ellipsometer.
4. Wafers were primed for photoresist coating using Hexamethyl-1,1,1,3,3,3-disilazane (HMDS) under vacuum for 5 minutes.
5. Wafers were spin-coated with (3 ml vol. on wafer, 4000 rpm, 25 s) positive photoresist, AZ5214E. Wafer hard-baked (120° C.) in oven for 10 minutes.
6. The other side of the wafers spin-coated with photoresist as before. Wafers were then soft-baked (90° C.) for 30 minutes.
7. The side of the wafers coated with soft-baked photoresist was exposed to UV light for 5 seconds through the appropriate mask. Exposed regions of photoresist were removed in development solution for 50–60 s. Wafers were rinsed in water and dried in $N_2$.
8. Wafers were then hard-baked in an 120° C. oven for 30 minutes to fix the remaining photoresist on the wafer.
9. Exposed oxide on the wafer was etched in BHF (40% $NH_4F$: 50% HF, 10:1). Wafers were then rinsed in $H_2O$ for 10 minutes. Complete removal of oxide was confirmed using an optical microscope.
10. Photoresist was removed from the silicon surface by sonication in acetone for 5 minutes, followed by immersion in isopropanol and rinsing in $H_2O$.
11. Etching of the exposed silicon, through the wafers was then carried out in 25% (v/v) tetramethylammonium-hydroxide (TMAH) at 85° C. and 25% (v/v) potassium hydroxide (KOH) at 65° C.
12. After etching, the wafers were rinsed in water and dried.
13. The surface oxide was removed by etching in BHF (40% $NH_4F$: 50% HF, 10:1). The wafers were again rinsed in water and dried.
14. Electrodes were then made by cutting the wafers into 4 mm×7 mm pieces around the etched regions.

Figure 14:
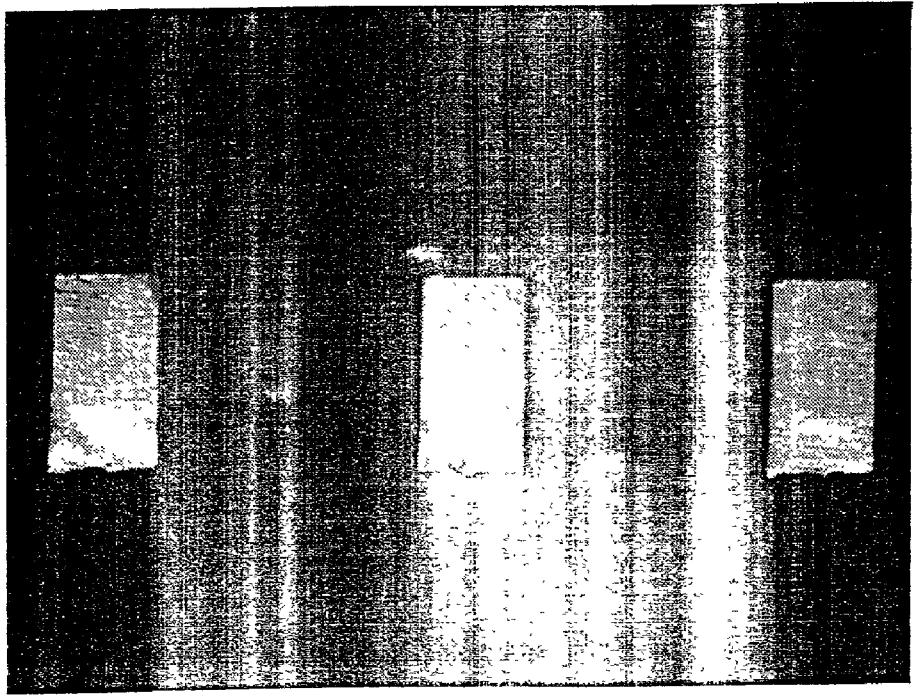
FIG. 14. Photograph of (100) silicon etched in TMAN or 25% (v/v) KOH at 85° C., illustrating the channels formed by this chemical treatment. Channel walls have a slope at 54.7° C.

FIG. 14. displays a side-view of a through-wafer etched (110) silicon electrode chip produced by this chemical treatment that has been cut by sawing from the middle of the chip to allow the photography.

The analogous channeled structures produced by sawing were also fabricated by wet etching when double-side-polished (110) wafers were used as a source of working electrodes.

Figure 15:
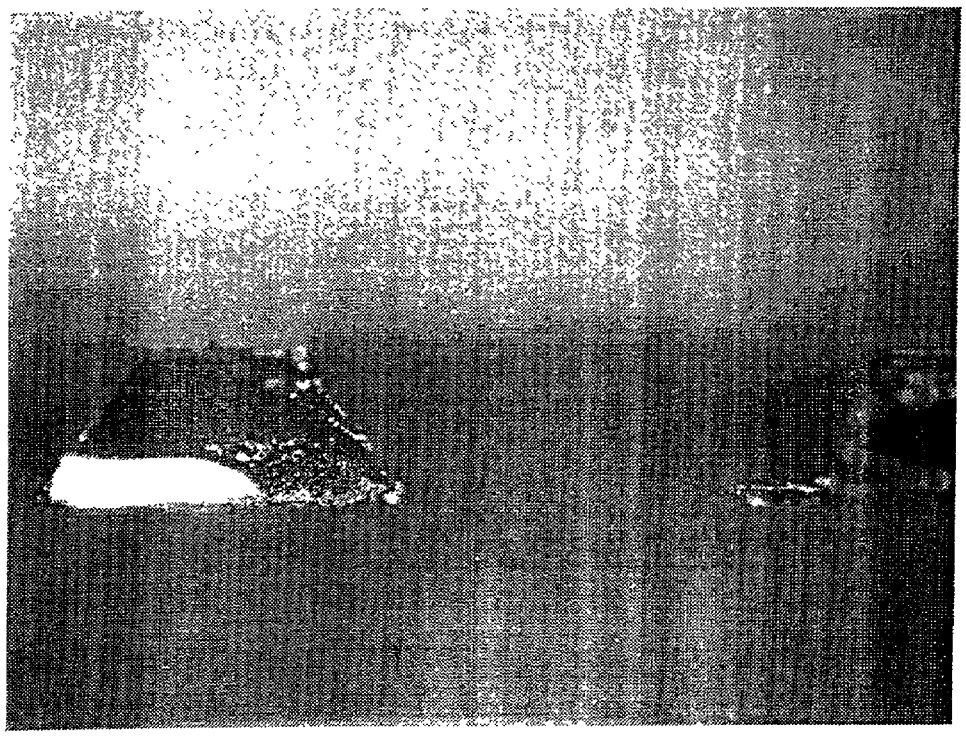
FIG. 15: Photograph of (110) silicon etched in 25% TMAH or KOH at 85° C., illustrating the channels formed by this chemical treatment. Channel walls have a slope at 54.7° C.

Fabrication Protocol.
1. Substrate: (100) silicon wafers, 0.02–0.03 $\Omega$cm, 380 $\mu$m thick, double side polished.
2. Wafers were cleaned in RCA1 ($H_2O$: 31% $H_2O_2$: 25% $NH_4OH$, 5:1:1) at 80° C. for 10 minutes, RCA2 ($H_2O$: 31% $H_2O_2$: 37% HCl, 5:1:1) at 80° C. for 15 minutes and dipped in HF for 30 seconds before drying in $N_2$.
3. Wafers were wet oxidised for 2 hours at 1000° C. Resultant oxide thickness was approximately 280 $\mu$m as measured with an ellipsometer.
4. Wafers were primed for photoresist coating using Hexamethyl-1,1,1,3,3,3,disilazane (HMDS) under vacuum for 5 minutes.
5. Wafers were spin-coated with (3 ml vol. on wafer, 4000 rpm, 25 s) positive photoresist, AZ5214E. Wafers were then hard-baked (120° C.) in an oven for 10 minutes.
6. The other side of the wafers were spin-coated with photoresist as before. Wafers were soft-baked (90° C.) for 30 minutes.
7. The side of the wafers coated with soft-baked photoresist was exposed to UV light for 5 seconds through the appropriate mask. Exposed regions of photoresist removed in development solution for 50–60 s. Wafer rinsed in water and dried in $N_2$.
8. Wafers were then hard-baked in 120° C. oven for 30 minutes to fix the remaining photoresist on the wafer.
9. Exposed oxide on the wafers was etched in BHF (40% $NH_4F$: 50% HF, 10:1). Wafers were then rinsed in $H_2O$ for 10 minutes. Complete removal of oxide was confirmed using optical microscope.
10. Photoresist was removed from the silicon surface by sonication in acetone for 5 minutes, followed by immersion in isopropanol and rinsing in $H_2O$.
11. Etching of the exposed silicon, through the wafer was then carried out in 25% (v/v) TMAH at 85° C. or 25% (v/v) KOH at 65° C.
12. After etching, the wafers were rinsed in water and dried.
13. The surface oxide was removed by etching in BHF (40% $NH_4F$: 50% HF, 10:1). The wafers were again rinsed in water and dried.
14. Electrodes were then made by cutting the wafer into approximately 8–9 mm×8–9 mm pieces around the etched regions FIG. 15. displays a side-view of a through-wafer etched (100) silicon electrode chip produced by this chemical treatment that has been cut by sawing from the middle of the chip to allow the photography.

Manufacture of Optically Transparent Cathode Chip by Coating a Si-wafer with SU-8 Resist Layers on Both Sides and Grooved by Sawing.

1. n-type or p-type (100, 111, or 110) 525 µm thick silicon wafers (0.01–0.02 Ωcm), double side polished were cleaned in RCA1 ($H_2O$: 31% $H_2O_2$: 25% $NH_4OH$, 5:1:1) at 80° C. for 10 minutes, RCA2 ($H_2O$: 31% $H_2O_2$: 37% HCl, 5:1:1) at 80° C. for 15 minutes and dipped in HF for 30 seconds before drying in $N_2$.
2. Wafers were then dehydrated for 2 hours in an oven at 120° C.
3. 5 ml of SM 1070, SU-8 based photoepoxy was applied to the surface of one side of the silicon wafers. The silicon wafers were spun at a rate of 500 rpm for 25 s to yield a coating of approximately 70 µm SU-8 on the silicon surface.
4. The solvents in the SU-8 were removed and the resist somewhat hardened by incubation of the wafer in an oven at 90° C. for 30 mins.
5. The SU-8 was then exposed to UV light for 25 seconds to cure and placed again in the oven at 90° C. for 5 minutes.
6. 5 ml of SM 1070, SU-8 based photoepoxy was applied to the surface of the uncoated side of the silicon wafers. The silicon wafers were spun at a rate of 500 rpm for 25 s to yield a coating of approximately 70 µm SU-8 on the silicon surface.
7. The solvents in the SU-8 were removed and the resist somewhat hardened by incubation of the wafer in an oven at 90° C. for 30 mins.
8. Another 5 ml of SM 1070, SU-8 based photoepoxy was applied to the surface of the same side of the silicon wafers. The silicon wafers were spun at a rate of 500 rpm for 25 s to yield a coating of approximately 70 µm SU-8 on the silicon surface. The wafers were again placed in an oven at 90° C. for 30 mins.
9. Step 8 was repeated another five times to yield an eventual SU-8 thickness of approximately 500 µm on the wafer surface.
10. This surface was cured by exposure to UV light for 160 seconds. The wafer was then again placed in the oven at 90° C. for 30 minutes.
11. Grooves were cut into the 70 µm thick SU-8 and silicon wafers using a Loadpoint Microace 3, series 3 saw and 20 µm wide blade. Spindle rotation speed was 15 rpm and cutting speed was 3 mm/s. Cutting steps of 60 µm were used. Sawing was carried out such that the base of the grooves formed were approximately 50 µm deep into the 500 µm thick SU-8, i.e. the blade cut entirely through the 70 µm thick SU-8 and silicon.
13. After formation of the grooves, the entire structure including the glass, SU-8 and silicon was cut e.g. to 7 mm×4 mm dimensions.
14. The optically transparent cathode chip can now be integrated to the different types of measuring cells.
15. Optionally, a counter electrode of equivalent size (section of silicon in photo) was then joined to the 7 mm×4 mm structures, via the SU-8.

The 70 µm thick SU-8 acts as an insulator between the working and counter electrodes. It also serves to join the counter electrode to the remainder of the cell. The 500 µm thick SU-8 layer acts as an electrically inert, transparent mechanical support for the silicon.

Anodic oxidation of the working electrodes. The grooved working electrodes were washed with acetone for 1 min, with isopropanol for 10 min, with 5% HF for 5 min and rinsed with water. After the washing procedure, the working electrodes were oxidized anodically one by one to have an oxide layer of ca. 1.0 nm. The anodic oxidation was carried out first galvanostatically up to the anodization potential of 2.94 V followed by potentiostatic anodization until the cell current diminished below 10 µA. The oxidation solution was 0.5 M $H_3BO_3$ adjusted to pH 7.0 with $NH_3$. After this, the working electrodes were rinsed with quartz distilled water.

Construction of the measurement cell. The anodized working electrodes were coated with a catching antibody layer as in Example 8. Thereafter, the flow-through cell was constructed inside the measurement cell by combining the optically transparent working electrodes with polished stainless steel sheet counter electrodes.

Figure 16:
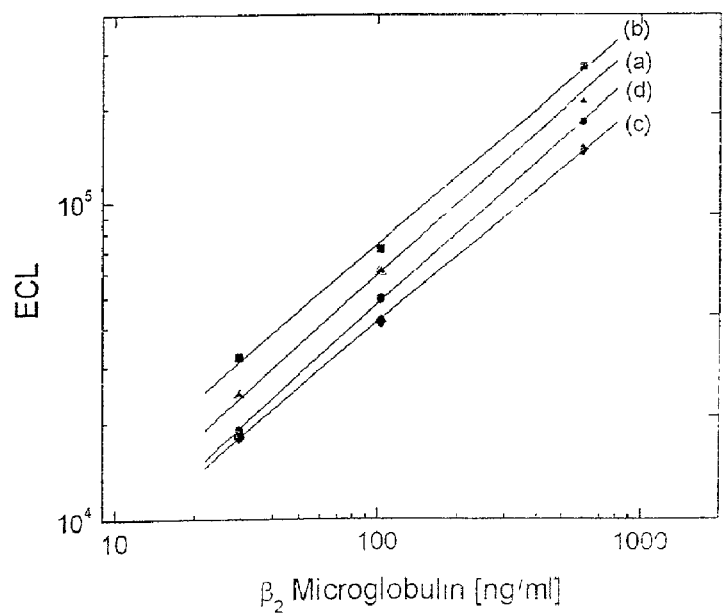
FIG. 16. Calibration curves of immunoassays of $\beta_2$-microglobulin in cells constructed from polished stainless steel counter electrode plates and, (a) optically transparent cathode chip by bonding glass on Si-wafer which is subsequently coated with SU-8 resist layer and grooved by sawing, (b) a cathode chip with grooving made by through-wafer wet etching of (110) silicon, (c) a cathode chip with grooving made by through-wafer wet etching of (100) silicon, and (d) by a cathode chip which was based on both side coating of a wafer with SU-8 and grooving by sawing.

Immunoassays of $\beta_2$-microglobulin. The immunoassays were carried out as in Example 8, except that the electrical excitation was carried out using coulostatic pulse generator (20 µC pulses, pulse voltage –20 V, pulse frequency 50 Hz, delay time 0.1 ms and gate time 3.0 ms. FIG. 16 displays immunoassays in cells constructed from polished stainless steel counter electrode plates and, (a) optically transparent cathode chip by bonding glass on Si-wafer which is subsequently coated with SU-8 resist layer and grooved by sawing, (b) a cathode chip with grooving made by through-wafer wet etching, of(110) silicon, (c) a cathode chip with grooving made by through-wafer wet etching of (100) silicon, and (d) by a cathode chip which was based on both side coating of a wafer with SU-8 and grooving by sawing.

EXAMPLE 10

Channeled Insulator Electrode Device Having a Single Integrated Cathode- and Anode Chip and an Immunoassay of $\beta_2$-Microglobulin Fabrication of Integrated Cathode and Anode Chip
1. A silicon dioxide layer of thickness 350 nm was thermally applied on double side polished silicon wafers (110), 0.01–0.02 Ωcm, thickness 350 µm. The wafers were then primed for coating with photoresist using HMDS for 5 minutes under vacuum. Positive photoresist was spin coated on the wafers using a spin rate of 500 rpm for 5 seconds followed by 4000 rpm for 25 seconds.
2. The wafers were then soft baked at 90° C. for 30 minutes to evaporate the solvents from the resist. The wafers were exposed to UV light through an appropriate mask for 4 seconds followed by development in the appropriate solution. The wafers were then hard baked in an oven at 120° C. for 30 minutes to fix the photoresist to the wafers.
3. The exposed silicon dioxide layer was then etched in BHF (40% $NH_4F$: 50% HF, 10:1) and the photoresist was removed using acetone with sonication for 10 minutes followed by rinsing in water.
4. The exposed silicon was then etched with 25% (v/v) TMAH at 85° C. or 25% (v/v) KOH at 65° C. to form 150 µm deep grooves.
5. The grooves were then filled with gold metal either by sputtering or electrochemical deposition.
6. The lower surface of the silicon wafers was coated with photoresist. The wafer was then soft baked at 90° C. for 30 minutes. The resist was then exposed to UV light for 4 seconds through an appropriate mask for 4 seconds followed by development in the appropriate solution. Wafers were hard-baked in an oven at 120° C. for 30 minutes to fix the photoresist on the wafer. The silicon dioxide layer on the upper (etched) surface and the exposed oxide on the top surface were removed using BHF (40% NH$_4$F: 50% HF, 10:1). Wafers were then rinsed in H$_2$O for 10 minutes. Complete removal of oxide was confirmed using an optical microscope. Photoresist was removed from the silicon surface by sonication in acetone for 5 minutes, followed by immersion in isopropanol and rinsing in H$_2$O.

7. An aluminium layer was then sputtered onto the lower surface of the silicon wafer to increase the conductivity of the wafer during bonding to the glass wafer.
8. Wafers were then bonded to glass wafers for support via their top surface (where the gold was deposited).
9. The aluminium layer was then removed.
10. The exposed silicon was then etched with 25% (v/v) TMAH at 85° C. or 25% (v/v) KOH at 65° C. to expose the gold pillars on the glass support and form silicon pillars between the gold structures.
11. The surface of the glass was then metallised by aluminium evaporation. Holes were drilled through the glass and electrical contacts were made to the gold pillars from the aluminium surface.

Figure 17:
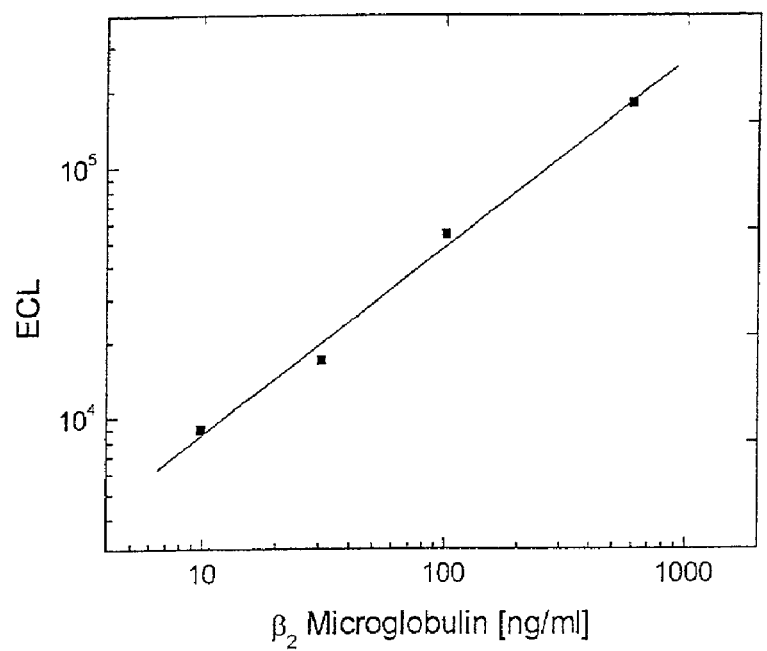
FIG. 17. A calibration curve of an immunometric immunoassay of $\beta_2$-microglobulin in a channeled insulator electrode device having integrated anodes and cathode in the same electrode chip.

Immunoassay of $\beta_2$-microglobulin. The working electrodes were anodized as in Example 9. Immunoassay was carried out as in Example 8, except that the electrical excitation was carried out using coulostatic pulsegenerator (20 μC pulses, pulse voltage −20 V, pulse frequency 50 Hz, delay time 0.1 ms and gate time 3.0 ms. FIG. 17 displays a calibration plot of immunometric immunoassay of $\beta_2$-microglobulin.

EXAMPLE 11

Figure 18:
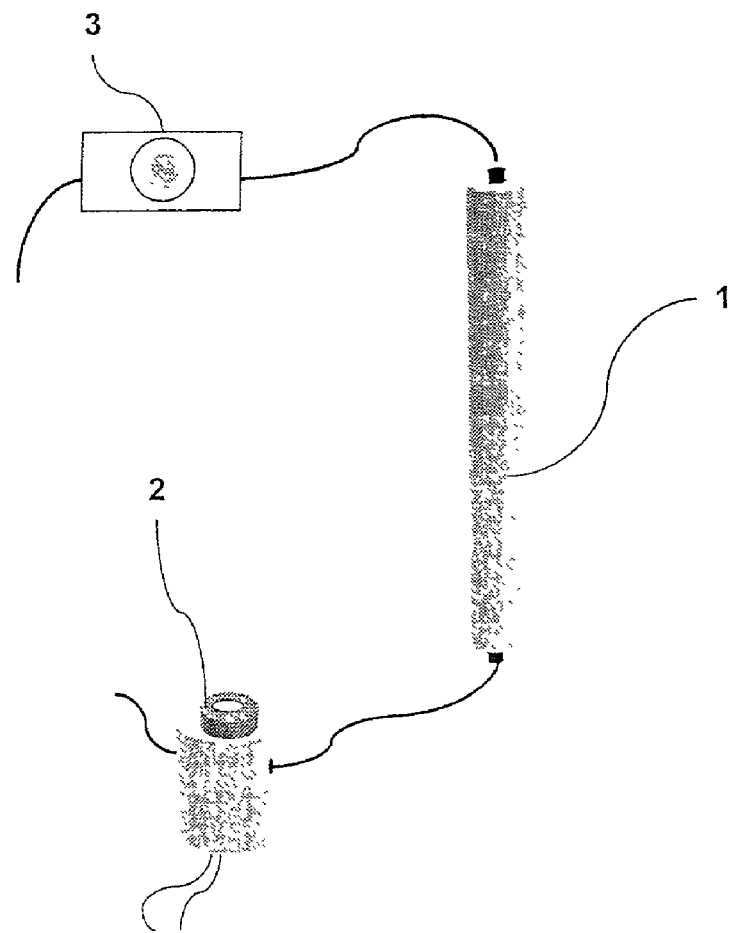
FIG. 18. A diagram of chromatographic set up utilizing a channeled insulator electrode as a detector. (1) Peristaltic pump, (2) Sephadex G-25-column (0.9×2.8 cm), (3) channeled insulator electrode as a detector of electrochemiluminescent species.
Figure 19:
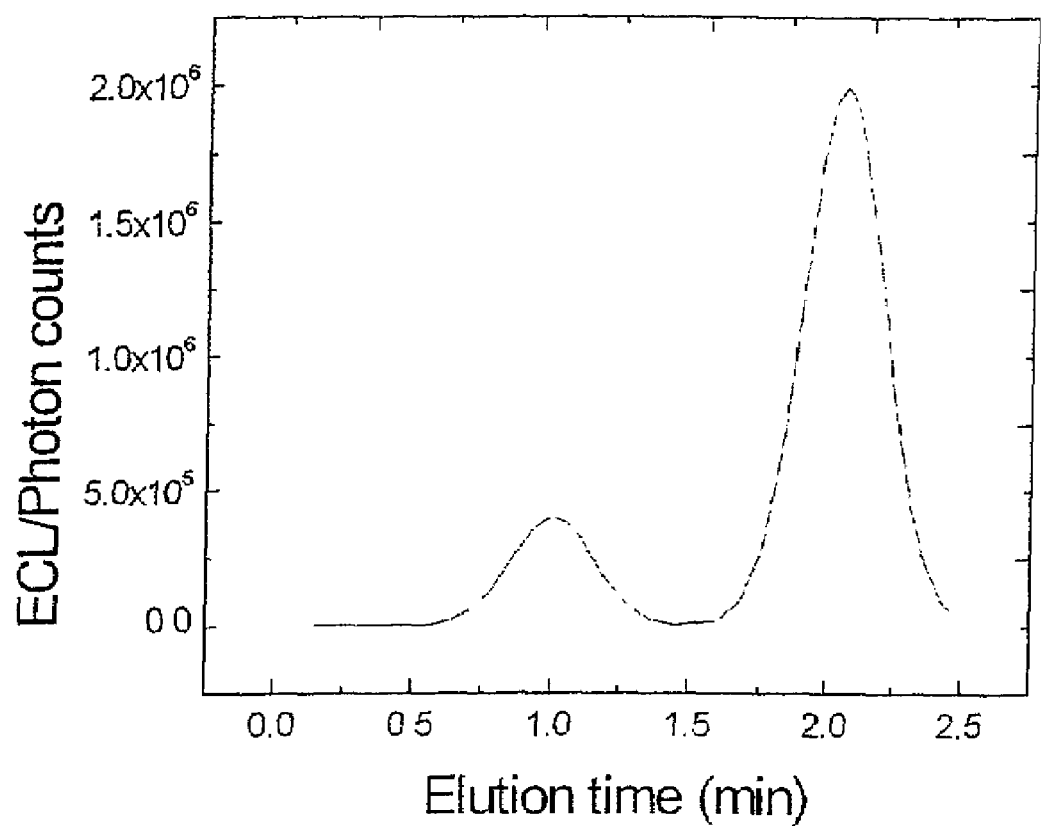
FIG. 19. A chromatogram of separation of labeled antibody and unreacted Tb(III)-1 label with Sephadex G-25 column as monitored by electrochemiluminescence generated in accordance with FIG. 18.

Channeled insulator electrode device used as a chromatographic detector. A labeled antibody and unreacted Tb(III) chelate label were separated with gel filtration and the flow was monitored by electrochemiluminescence. Mouse antibody to human CRP (Medix Biochemica, Finland, clone 6404) was labeled with Tb(III)-1 chelate in the same way as in Example 7. The labeled antibody was separated from unreacted chelate with Sephadex G-25-column (0.9×2.8 cm) using 0.5 mol/L borate buffer, pH 8.0 as an eluent. Separation was monitored using a flow-through insulator electrode device similar to those used in the Example 9 (a) and an electrochemiluminometer with settings: pulse frequency 50 Hz, pulse charge 100 μC, pulse voltage −30 V, delay time 0.1 ms and window time 3 ms (FIG. X). FIG. 18 displays the instrument setup and FIG. 19 chromatogram of the separation experiment.

EXAMPLE 12

Figure 20:
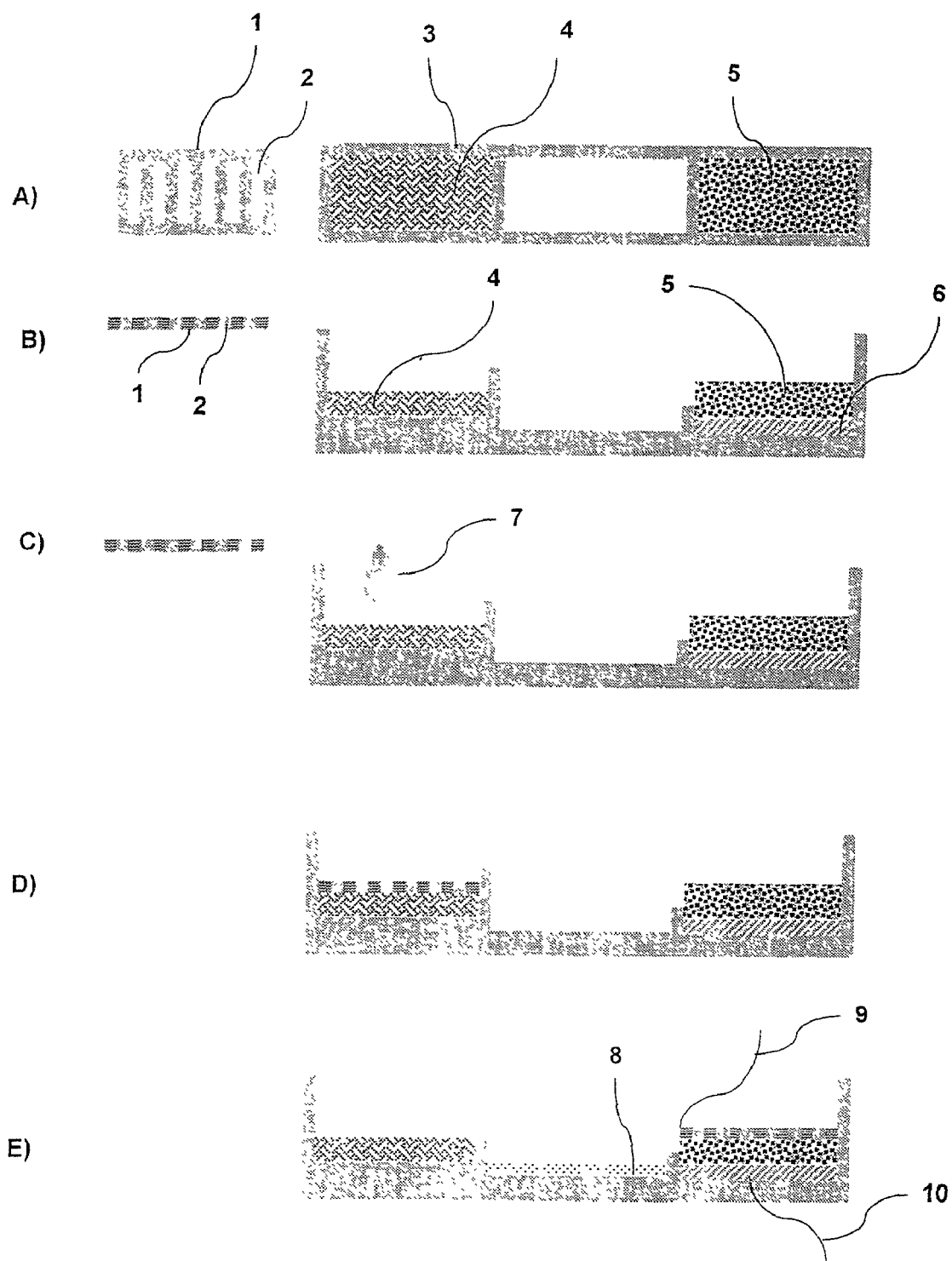
FIG. 20. Channeled insulator electrode device not needing an external pump. (1) Silicon chip (size 0.5×4×7 mm), (2) Etched channels (30 µm×3 mm), (3) Plastic device, (4) Labeled antibody pad, (5) Sponge with washing and measuring buffer, (6) Anode, stainless steel, (7) Sample (serum or plasma) 20 µL, (8) Washing solution overflow, (9) Contact to cathode, (10) Contact to anode.
Figure 21:
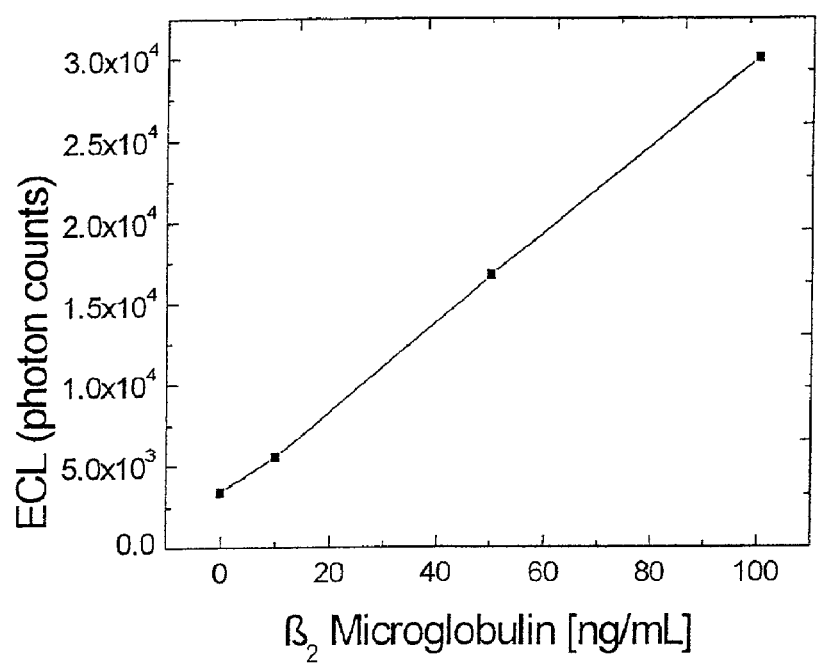
FIG. 21. A calibration curve of an immunometric immunoassay of $\beta_2$-microglobulin with the devices of FIG. 20.

An insulator electrode device based on dry chemistry and a flow system not needing an external pump. Through-etched (110) silicon electrodes (0.5×4×7 mm, having channels of 30 μm×3 mm were fabricated as in Example 9. Coating of the electrodes, preparation of labeled antibody, and prearation of standards for $\beta_2$-microglobulin assay were done in the same way as in Example 8. The assay was performed in a special device contracted from plastic (FIG. 20). Labeled antibody was dried on the pad (4). After drying 20 μl of standard was added over the pad and immunoreaction was started immediately by moving precoated silicon electrode over the pad. The channels were filled with the mixture of standard and labeled antibody. After five minutes the electrode was moved onto the sponge (5) full with washing and measuring buffer and pressed downwards. The washing solution goes now into the compartment (8). By connecting the electrodes (9, 10) to the pulse generator and keeping the electrode pressed, the electrochemiluminesce was measured in the same way as in Example 6. A typical standard curve is shown in FIG. 21.

EXAMPLE 13

Figure 22:
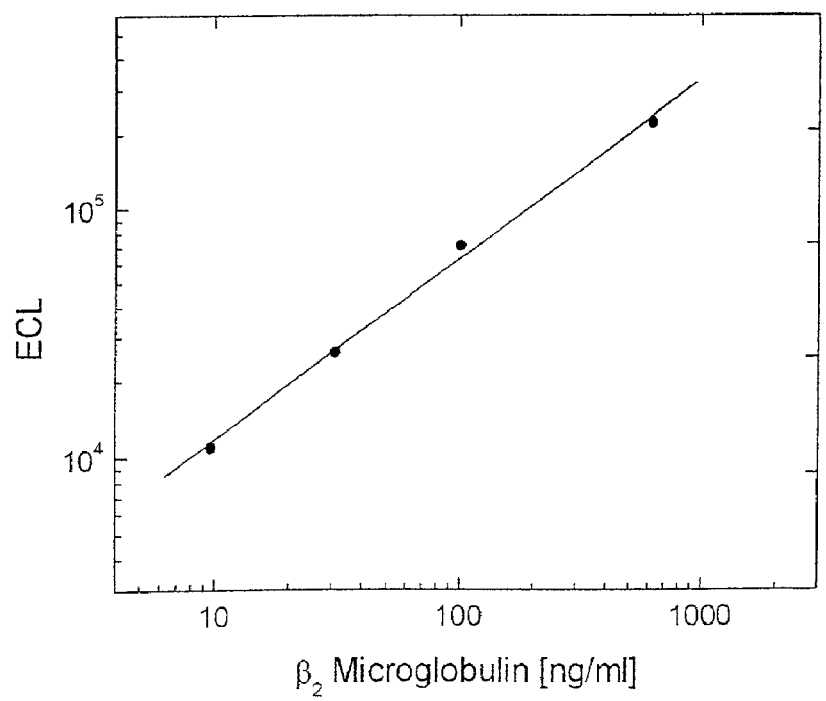
FIG. 22. A calibration curve of an immunometric immunoassay of $\beta_2$-microglobulin with channeled insulator electrode devices based on isotropic etching of (111) silicon and optically transparent ITO-coated glass counter electrodes.

Insulator Electrode Devices Composed of Optically Transparent Counter Electrodes and Grooved Non-transparent Working Electrodes Fabricated by Isotropic Etching, and an Immunoassay of $\beta_2$-microglobulin Fabrication Protocol.
1. n-type or p-type (100, 111, or 110) 380 μm or 525 μm thick silicon wafers (0.01–0.02 Ωcm), double side polished were cleaned in RCA1 (H$_2$0: 31% H$_2$O$_2$: 25% NH$_4$OH, 5:1:1) at 80° C. for 10 minutes, RCA2 (H$_2$0: 31% H$_2$O$_2$: 37% HCl, 5:1:1) at 80° C. for 15 minutes and dipped in HF for 30 seconds before drying in N$_2$.
2. Wafers were wet oxidised for 2 hours at 1000° C. Resultant oxide thickness was approximately 280 to 350 nm as measured with an ellipsometer.
3. Wafers were primed for photoresist coating using Hexamethyl-1,1,1,3,3,3-disilazane (HMDS) under vacuum for 5 minutes.
4. Wafers were spin-coated with (3 ml vol. on wafer, 4000 rpm, 25 s) positive photoresist, AZ5214E. Wafers were then hard-baked (120° C.) in an oven for 10 minutes.
5. The lower side of the wafers were spin-coated with photoresist. Wafers were soft-baked (90° C.) for 30 minutes.
6. The side of the wafers coated with soft-baked photoresist was exposed to UV light for 5 seconds through the appropriate mask. Exposed regions of photoresist removed in development solution for 50–60 s. Wafer rinsed in water and dried in N$_2$.
8. Wafers were then hard-baked in 120° C. oven for 30 minutes to fix the remaining photoresist on the wafer.
9. Exposed oxide on the wafers was etched in BHF (40% NH$_4$F: 50% HF, 10:1). Wafers were then rinsed in H$_2$O for 10 minutes. Complete removal of oxide was confirmed using optical microscope.
10. Photoresist was removed from the silicon surface by sonication in acetone for 5 minutes, followed by immersion in isopropanol and rinsing in H$_2$O.
11. Etching of the exposed silicon, through the wafer was then carried out in 3% (v/v) HNO$_3$/77% (v/v) CH$_3$COOH/22% (v/v). After etching, the wafers were rinsed in water and dried.
12. The surface oxide was removed by etching in BHF (40% NH$_4$F: 50% HF, 10:1). The wafers were again rinsed in water and dried.
13. Electrodes were then made by cutting the wafer into approximately 4 mm×7 mm pieces around the etched regions Immunoassay of $\beta_2$-microglobulin. The working electrodes were thermally oxidized as in Example 1. Immunoassay was carried out as in Example 8, except that the counter electrode was ITO-coated glass plate (Lohja Oy, Finland) and the electrical excitation was carried out in situ using coulostatic pulsegenerator (20 μC pulses, pulse voltage −20 V, pulse frequency 50 Hz, delay time 0.1 ms and gate time 3.0 ms. FIG. 22 displays a calibration plot of immunometric immunoassay of $\beta_2$-microglobulin.

EXAMPLE 14

Figure 23:
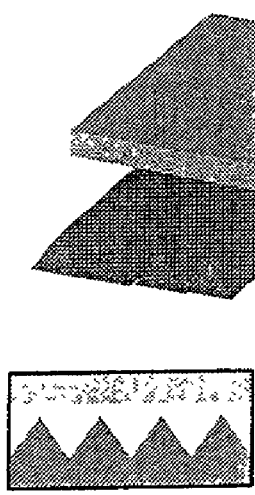
FIG. 23. A channeled insulator electrode device composed of unisotropically etched (100) silicon and ITO-glass electrode.

Insulator Electrode Devices Composed of Optically Transparent Counter Electrodes and Grooved Non-transparent Working Electrodes Fabricated by Anisotropic Etching, and an Immunoassay of $\beta_2$-microglobulin Fabrication Protocol.
1. Substrate: (100) silicon wafers, 0.02–0.03Ωcm, 525 μm thick, double side polished.
2. Wafers were cleaned in RCA1 ($H_2O$: 31% $H_2O_2$: 25% $NH_4OH$, 5:1:1) at 80° C. for 10 minutes, RCA2 ($H_2O$: 31% $H_2O_2$: 37% HCl, 5:1:1) at 80° C. for 15 minutes and dipped in HF for 30 seconds before drying in $N_2$.
3. Wafers were wet oxidised for 2 hours at 1000° C. Resultant oxide thickness was approximately 280 μm as measured with an ellipsometer.
4. Wafers were primed for photoresist coating using Hexamethyl-1,1,1,3,3,3-disilazane (HMDS) under vacuum for 5 minutes.
5. Wafers were spin-coated with (3 ml vol. on wafer, 4000 rpm, 25 s) positive photoresist, AZ5214E. Wafers were then hard-baked (120° C.) in an oven for 10 minutes.
6. The lower side of the wafers were spin-coated with photoresist. Wafers were soft-baked (90° C.) for 30 minutes.
7. The side of the wafers coated with soft-baked photoresist was exposed to UV light for 5 seconds through the appropriate mask. Exposed regions of photoresist removed in development solution for 50–60 s. Wafer rinsed in water and dried in $N_2$.
8. Wafers were then hard-baked in 120° C. oven for 30 minutes to fix the remaining photoresist on the wafer.
9. Exposed oxide on the wafers was etched in BHF (40% $NH_4F$: 50% HF, 10:1). Wafers were then rinsed in $H_2O$ for 10 minutes. Complete removal of oxide was confirmed using optical microscope.
10. Photoresist was removed from the silicon surface by sonication in acetone for 5 minutes, followed by immersion in isopropanol and rinsing in $H_2O$.
11. Etching of the exposed silicon, into the wafer was then carried out in 25% (v/v) TMAH at 85° C. or 25% (v/v) KOH at 65° C. until the slow etching (111) planes restricted the etching further. After etching, the wafers were rinsed in water and dried.
12. The surface oxide was removed by etching in BHF (40% $NH_4F$: 50% HF, 10:1). The wafers were again rinsed in water and dried.
13. Electrodes were then made by cutting the wafer into approximately 4 mm×7 mm pieces around the etched regions FIG. 23 shows the triangle-shaped channels created with this procedure. The optically transparent counter electrode is on the top, and the grooved working electrode is at the bottom.

Figure 24:
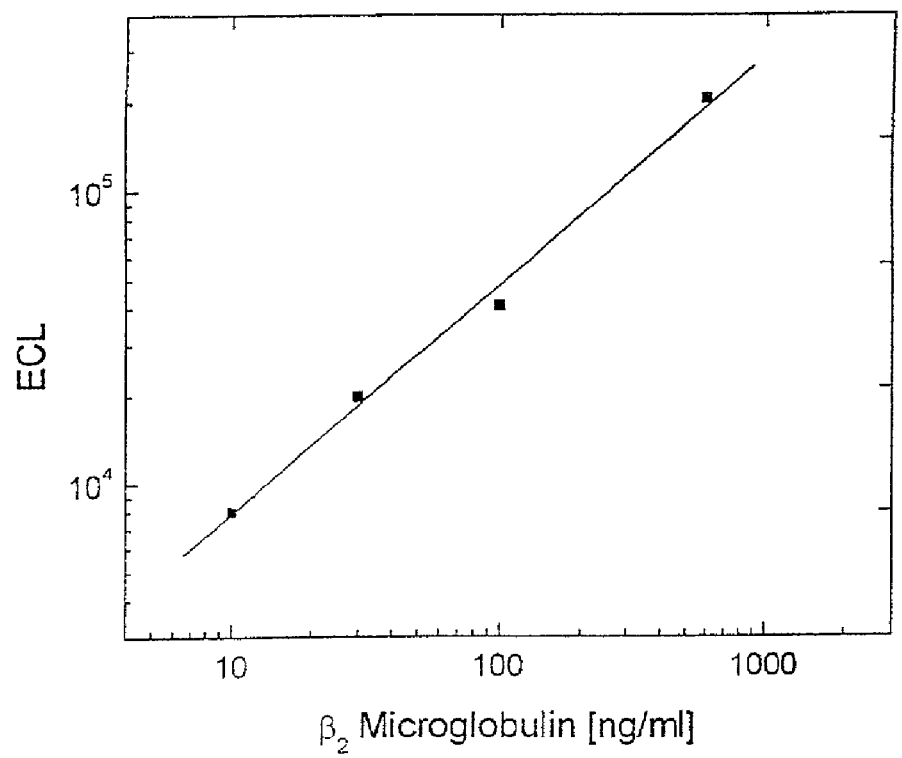
FIG. 24. A calibration curve of an immunometric immunoassay of $\beta_2$-microglobulin with channeled insulator electrode devices based on unisotropic etching of (100) silicon and optically transparent ITO-coated glass counter electrodes.

Immunoassay of $\beta_2$-microglobulin. The working electrodes were thermally oxidized as in Example 1. Immunoassay was carried out as in Example 8, the counter electrode was ITO-coated glass plate (Lohja Oy, Finland) and the electrical excitation was carried out using coulostatic pulsegenerator (20 μC pulses, pulse voltage −20 V, pulse frequency 50 Hz, delay time 0.1 ms and gate time 3.0 ms. FIG. 24 displays a calibration plot of immunometric immunoassay of $\beta_2$-microglobulin.

What is claimed is:

1. An insulating film-coated electrode for producing electrogenerated chemical reactions in a reaction medium, the electrode comprising:
    an electrically conductive material, at least a portion of the surface of which is coated with an electrically insulating film,
    wherein the surface of the electrically conductive material has a plurality of channels to provide a high specific surface area for the electrode, and
    wherein the surface of the electrode is such as to provide for a diffusion distance of 10 nm to 1 mm in the reaction medium.

2. The electrode according to claim 1, wherein the high specific surface area means an area which is at least 1.5 times the surface area of a corresponding, non-channeled electrode.

3. The electrode according to claim 1, wherein the channeled electrode comprises microstructures in the form of microchannels, canals, grooves, trenches, spikes, pillars, columns or pores, or the like.

4. The electrode according to claim 1, wherein the electrode comprises an array of high-aspect ratio walls or columns, arranged in rows, or dendrimetric types of structures.

5. The electrode according to any one of claims 1, wherein the electrically conductive material is channeled n- or p-type silicon.

6. The electrode according to claim 1, wherein the conductive material is a metal, a conductive oxide or a conductive polymer.

7. The electrode according to claim 5, wherein the electrically insulating film is silicon dioxide.

8. An insulator electrode device comprising a channeled or microstructured electrode as defined in any of the claims 1 as a working electrode.

9. An insulator electrode device comprising a channeled or microstructured electrode as defined in any of the claims 1 as a working electrode, positioned between two current delivering electrodes in a solution and an electric field, but out of electronic contact with said electrodes.

* * * * *